(12) United States Patent
Connelly et al.

(10) Patent No.: US 8,372,846 B2
(45) Date of Patent: Feb. 12, 2013

(54) CO-CRYSTALS AND PHARMACEUTICAL COMPOSITIONS COMPRISING THE SAME

(75) Inventors: Patrick R. Connelly, Harvrad, MA (US); Sherry Collier, Flemington, NJ (US); Michael Tauber, Allston, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 13/269,841

(22) Filed: Oct. 10, 2011

(65) Prior Publication Data

US 2012/0088740 A1   Apr. 12, 2012

Related U.S. Application Data

(62) Division of application No. 11/711,213, filed on Feb. 27, 2007, now Pat. No. 8,039,475.

(60) Provisional application No. 60/777,221, filed on Feb. 27, 2006.

(51) Int. Cl.
*A61K 31/4965* (2006.01)

(52) U.S. Cl. ............................... 514/255.05; 514/255.06

(58) Field of Classification Search .............. 514/255.05
See application file for complete search history.

(56) References Cited

U.S. PATENT DOCUMENTS

| | | | |
|---|---|---|---|
| 4,499,082 A | 2/1985 | Shenvi et al. |
| 4,720,484 A | 1/1988 | Vincent et al. |
| 4,880,780 A | 11/1989 | Trainor et al. |
| 5,053,519 A | 10/1991 | Teetz et al. |
| 5,231,084 A | 7/1993 | Hock et al. |
| 5,371,072 A | 12/1994 | Webb et al. |
| 5,384,410 A | 1/1995 | Kettner |
| 5,468,858 A | 11/1995 | Berlin et al. |
| 5,484,801 A | 1/1996 | Al-Razzak et al. |
| 5,496,927 A | 3/1996 | Kolb et al. |
| 5,502,061 A | 3/1996 | Hui et al. |
| 5,559,158 A | 9/1996 | Al-Razzak et al. |
| 5,610,193 A | 3/1997 | Al-Razzak et al. |
| 5,656,600 A | 8/1997 | Abelman et al. |
| 5,656,627 A | 8/1997 | Bemis et al. |
| 5,672,582 A | 9/1997 | Veber et al. |
| 5,716,929 A | 2/1998 | Bemis et al. |
| 5,725,878 A | 3/1998 | Al-Razzak et al. |
| 5,736,520 A | 4/1998 | Bey et al. |
| 5,756,466 A | 5/1998 | Bemis et al. |
| 5,760,029 A | 6/1998 | Jadhav et al. |
| 5,807,876 A | 9/1998 | Armistead et al. |
| 5,847,135 A | 12/1998 | Bemis et al. |
| 5,849,866 A | 12/1998 | Kolb |
| 5,861,267 A | 1/1999 | Su |
| 5,866,684 A | 2/1999 | Attwood et al. |
| 5,948,436 A | 9/1999 | Al-Razzak et al. |
| 5,973,111 A | 10/1999 | Bemis et al. |
| 5,990,276 A | 11/1999 | Zhang et al. |
| 6,018,020 A | 1/2000 | Attwood et al. |
| 6,025,147 A | 2/2000 | Bemis et al. |
| 6,025,516 A | 2/2000 | Ramaswamy et al. |
| 6,037,157 A | 3/2000 | Norbeck |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bemis et al. |
| 6,117,639 A | 9/2000 | Germann et al. |
| 6,130,315 A | 10/2000 | Kolb |
| 6,143,715 A | 11/2000 | Llinas-Brunet et al. |
| 6,153,579 A | 11/2000 | Kim et al. |
| 6,172,077 B1 | 1/2001 | Curtis et al. |
| 6,183,121 B1 | 2/2001 | Kim et al. |
| 6,211,338 B1 | 4/2001 | Malcolm et al. |
| 6,225,320 B1 | 5/2001 | Kulagowski et al. |
| 6,251,583 B1 | 6/2001 | Zhang et al. |
| 6,265,380 B1 | 7/2001 | Tung et al. |
| 6,268,207 B1 | 7/2001 | Bailey et al. |
| 6,274,613 B1 | 8/2001 | Plant et al. |
| 6,303,287 B1 | 10/2001 | Kim et al. |

(Continued)

FOREIGN PATENT DOCUMENTS

DE   3211676   10/1983
EP   0417721   3/1991

(Continued)

OTHER PUBLICATIONS

Almarsson et al "Crystal engineering of the composition of pharmaceutical phases. Do pharmaceutical co-crystals represent a new path to improved medicines" Chemical Comm. (2004) pp. 1889-1896.

(Continued)

*Primary Examiner* — Brian McDowell
(74) *Attorney, Agent, or Firm* — Honigman Miller Schwartz and Cohn; Kathryn D. Soulier; Jonathan P. O'Brien

(57) ABSTRACT

The invention relates to compositions and co-crystals each comprising (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide having the structure:

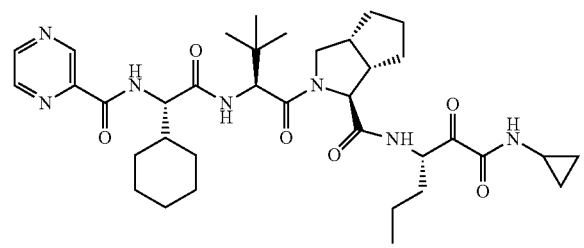

and the co-crystal former 4-amino salicylic acid. Also within the scope of this invention are methods of making and using the same.

10 Claims, 10 Drawing Sheets

U.S. PATENT DOCUMENTS

| | | |
|---|---|---|
| 6,322,847 B1 | 11/2001 | Zhong et al. |
| 6,323,180 B1 | 11/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Shi |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet et al. |
| 6,420,522 B1 | 7/2002 | Bemis et al. |
| 6,498,178 B2 | 12/2002 | Stamos et al. |
| 6,528,276 B1 | 3/2003 | Germann et al. |
| 6,534,523 B1 | 3/2003 | Llinas- Brunet et al. |
| 6,541,496 B1 | 4/2003 | Armistead et al. |
| 6,548,555 B1 | 4/2003 | Curatolo et al. |
| 6,569,195 B2 | 5/2003 | Yang et al. |
| 6,608,027 B1 | 8/2003 | Tsantrizos et al. |
| 6,608,067 B1 | 8/2003 | Tung et al. |
| 6,617,309 B2 | 9/2003 | Tung et al. |
| 6,653,127 B1 | 11/2003 | Malcolm et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena et al. |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,909,000 B2 | 6/2005 | Farmer et al. |
| 6,911,428 B2 | 6/2005 | Zhu et al. |
| 6,914,122 B2 | 7/2005 | Venkatraman et al. |
| 6,919,423 B2 | 7/2005 | Llinas-Brunet et al. |
| 7,012,066 B2 | 3/2006 | Saksena et al. |
| 7,109,172 B2 | 9/2006 | Britt et al. |
| 7,244,721 B2 | 7/2007 | Saksena et al. |
| 7,273,885 B2 | 9/2007 | Pitlik et al. |
| 7,288,624 B2 | 10/2007 | Bemis et al. |
| 7,365,092 B2 | 4/2008 | Cottrell et al. |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung et al. |
| 7,504,378 B2 | 3/2009 | Llinas-Brunet et al. |
| 7,592,316 B2 | 9/2009 | Njoroge et al. |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley et al. |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0119752 A1 | 6/2003 | Farmer et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris et al. |
| 2004/0067901 A1 | 4/2004 | Bhat et al. |
| 2004/0072788 A1 | 4/2004 | Bhat et al. |
| 2004/0077600 A1 | 4/2004 | Tung et al. |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet |
| 2004/0266731 A1 | 12/2004 | Tung et al. |
| 2005/0020503 A1 | 1/2005 | Llinas-Brunet et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine et al. |
| 2005/0197301 A1 | 9/2005 | Njoroge et al. |
| 2005/0215486 A1 | 9/2005 | Cottrell et al. |
| 2005/0222236 A1 | 10/2005 | Tsantrizos et al. |
| 2005/0249702 A1 | 11/2005 | Njoroge et al. |
| 2005/0287514 A1 | 12/2005 | Byrn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui et al. |
| 2006/0105978 A1 | 5/2006 | Chu et al. |
| 2006/0205672 A1 | 9/2006 | Saksena et al. |
| 2006/0211629 A1 | 9/2006 | Britt et al. |
| 2007/0087973 A1 | 4/2007 | Tanoury |
| 2007/0105781 A1 | 5/2007 | Lyons et al. |
| 2007/0161789 A1 | 7/2007 | Cottrell et al. |
| 2007/0179167 A1 | 8/2007 | Cottrell et al. |
| 2007/0191381 A1 | 8/2007 | Tung |
| 2007/0212683 A1 | 9/2007 | Connelly |
| 2007/0218012 A1 | 9/2007 | Bittorf et al. |
| 2007/0218138 A1 | 9/2007 | Bittorf et al. |
| 2007/0225297 A1 | 9/2007 | Perni et al. |
| 2007/0231262 A1 | 10/2007 | Lin et al. |
| 2007/0243166 A1 | 10/2007 | Llinas-Brunet et al. |
| 2007/0244334 A1 | 10/2007 | Tanoury et al. |
| 2007/0292933 A1 | 12/2007 | Pitlik et al. |
| 2008/0045480 A1 | 2/2008 | Farmer et al. |
| 2008/0070972 A1 | 3/2008 | Kadiyala et al. |
| 2008/0125376 A1 | 5/2008 | Cottrell et al. |
| 2008/0167480 A1 | 7/2008 | Wallace |
| 2008/0267915 A1 | 10/2008 | Lin et al. |
| 2008/0311079 A1 | 12/2008 | Perni et al. |
| 2009/0022688 A1 | 1/2009 | Farmer et al. |
| 2009/0143312 A1 | 6/2009 | Tung et al. |
| 2009/0191555 A1 | 7/2009 | Lin et al. |
| 2009/0247468 A1 | 10/2009 | Bittorf et al. |

FOREIGN PATENT DOCUMENTS

| | | |
|---|---|---|
| EP | 0675112 | 10/1995 |
| JP | 09124691 | 5/1997 |
| WO | WO 92/12140 | 7/1992 |
| WO | WO 93/25574 | 12/1993 |
| WO | WO 94/14436 | 7/1994 |
| WO | WO 95/07696 | 3/1995 |
| WO | WO 95/09614 | 4/1995 |
| WO | WO 96/11697 | 4/1996 |
| WO | WO 97/17364 | 5/1997 |
| WO | WO 97/40028 | 10/1997 |
| WO | WO 97/43310 | 11/1997 |

| | | |
|---|---|---|
| WO | WO 98/13365 | 4/1998 |
| WO | WO 98/17679 | 4/1998 |
| WO | WO 98/22496 | 5/1998 |
| WO | WO 98/40381 | 9/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/09543 | 2/2000 |
| WO | WO 00/09558 | 2/2000 |
| WO | WO 00/09588 | 2/2000 |
| WO | WO 00/23421 | 4/2000 |
| WO | WO 00/31129 | 6/2000 |
| WO | WO 00/56331 | 9/2000 |
| WO | WO 00/59929 | 10/2000 |
| WO | WO 01/02424 | 1/2001 |
| WO | WO 01/07407 | 2/2001 |
| WO | WO 01/32691 | 5/2001 |
| WO | WO 01/40262 | 6/2001 |
| WO | WO 01/40266 | 6/2001 |
| WO | WO 01/58929 | 8/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/07761 | 1/2002 |
| WO | WO 02/08187 | 1/2002 |
| WO | WO 02/08198 | 1/2002 |
| WO | WO 02/08244 | 1/2002 |
| WO | WO 02/08251 | 1/2002 |
| WO | WO 02/08256 | 1/2002 |
| WO | WO 02/18369 | 3/2002 |
| WO | WO 02/48116 | 6/2002 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/074474 | 9/2003 |
| WO | WO 03/087092 | 10/2003 |
| WO | WO 2004/026896 | 4/2004 |
| WO | WO 2004/030670 | 4/2004 |
| WO | WO 2004/032827 | 4/2004 |
| WO | WO 2004/037855 | 5/2004 |
| WO | WO 2004/039833 | 5/2004 |
| WO | WO 2004/064762 | 8/2004 |
| WO | WO 2004/072243 | 8/2004 |
| WO | WO 2004/078161 | 9/2004 |
| WO | WO 2004/089974 | 10/2004 |
| WO | WO 2004/092161 | 10/2004 |
| WO | WO 2004/093798 | 11/2004 |
| WO | WO 2004/094452 | 11/2004 |
| WO | WO 2004/103996 | 12/2004 |
| WO | WO 2004/113365 | 12/2004 |
| WO | WO 2005/007681 | 1/2005 |
| WO | WO 2005/010029 | 2/2005 |
| WO | WO 2005/021584 | 3/2005 |
| WO | WO 2005/028501 | 3/2005 |
| WO | WO 2005/028502 | 3/2005 |
| WO | WO 2005/030796 | 4/2005 |
| WO | WO 2005/035525 | 4/2005 |
| WO | WO 2005/037214 | 4/2005 |
| WO | WO 2005/037860 | 4/2005 |
| WO | WO 2005/042570 | 5/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/058821 | 6/2005 |
| WO | WO 2005/070955 | 8/2005 |
| WO | WO 2005/073195 | 8/2005 |
| WO | WO 2005/073216 | 8/2005 |
| WO | WO 2005/077969 | 8/2005 |
| WO | WO 2005/085242 | 9/2005 |
| WO | WO 2005/085275 | 9/2005 |
| WO | WO 2005/087721 | 9/2005 |
| WO | WO 2005/087725 | 9/2005 |
| WO | WO 2005/087731 | 9/2005 |
| WO | WO 2005/095403 | 10/2005 |
| WO | WO 2005/107745 | 11/2005 |
| WO | WO 2005/113581 | 12/2005 |
| WO | WO 2005/123076 | 12/2005 |
| WO | WO 2006/000085 | 1/2006 |
| WO | WO 2006/007448 | 1/2006 |
| WO | WO 2006/007700 | 1/2006 |
| WO | WO 2006/007708 | 1/2006 |
| WO | WO 2006/050250 | 5/2006 |
| WO | WO 2007/016589 | 2/2007 |
| WO | WO 2007/025307 | 3/2007 |
| WO | WO 2007/098270 | 8/2007 |
| WO | WO 2008/106058 | 9/2008 |

OTHER PUBLICATIONS

Anonymous, VPI internet press release Sep. 7, 2004.
Anonymous, newsrx internet article, May 31, 2004.
Arasappan, A., "Hepatitis C Virus NS3-4A Serine Protease Inhibitors: SAR of P'2 Moiety with Improved Potency", Bioorg. & Med. Chem. Let., vol. 15, (2005), pp. 4180-4184.
Avolio, S., "Inhibitors of hepatitis C virus NS3/4A: a-Ketoamide based macrocyclic inhibitors," Bioorganic & Medicinal Chemistry Letters (2009), 19, pp. 2295-2298.
Bastos, M., "Inhibitors of Human Heart Chymase Based on a Peptide Library", Proc. Natl. Acad. Sci. USA, vol. 92 (1995), pp. 6738-6742.
Beak, P., "Complex Induced Proximity Effects: Enantioselective Syntheses Based on Asymmetric Deprotonations of N-Boc-Pyrrolidines", J. Amer. Chem. Soc., vol. 116 (1994), pp. 3231-3239.
Behrens, C., "Selective Transformations of 2,3-Epoxy alcohols and Related Derivatives. Strategies for Nucleophilic Attack at Carbon-3 or Carbon-2", J. Org.Chem., vol. 50 (1985), pp. 5696-5704.
Bergmeier, S.C., "Synthesis of Bicyclic Proline Analogs Using a formal [3+2] Intramol ecular Aziridine-Allylsilane Cycloaddition Reaction", Tetrahedron, vol. 55, No. 26 (1999), pp. 8025-8038.
Blair, W., "5th Antiviral Drug Discovery and Development Summit," Expert opinion on investigational drugs (2004), 13 (8), pp. 1065-1069.
Blankley, C.J., "Synthesis and Structure-Activity Relationships of Potent New Abgiotensin Converting Enzyme Inhibitors Containing Saturated Bicyclic Amino Acids", J. of Medicinal Chem., vol. 30 (1987).
Cacciola, J., "The Synthesis of Lysine a-Ketoamide Thrombin Inhibitors via an Epoxy Amide Ring Opening", Tetrahedron Let., vol. 38, No. 33 (1977), pp. 5741-5744.
Chawla, et al., "Challenges in Polymorphism of Pharmaceuticals", CRIPS vol. 5, No. 1, Jan.-Mar. 2004, pp. 9-12.
Chen, S., "Synthesis and Evaluation of Tripeptidyl a-Ketoamides as Human Rhinovirus 3C Protease Inhibitors", Bioorg. & Med. Chem. Letters, vol. 13, No. 20 (2003), pp. 3531-3536.
Chen, S., "Discovery of Small-Molecule Inhibitors of HCV NS3-4A Protease as Potential Therapeutic Agents against HCV Infection," Current Medicinal Chemistry (2005), 12(20), pp. 2317-2342.
Chen, S., "P1 and P1' Optimization of [3,4]-Bicydoproline P2 Incorporated Tetrapeptidyl a-ketoamide Based HCV Protease Inhibitors," Letters in Drug Design and Discovery (2005), 2(2), pp. 118-123.
Cheng, W., "Stereoselective Synthesis of Unnatural Spiroisoxazolinoproline-Based Acids and Derivatives", J. Org. Chem., (2002), pp. 5673-5677.
Collado, I., "Stereocontrolled Synthesis of 4-Substituted (±)-Kainic Acids", Journal of Organic Chem., vol. 63 (1998).
Davis, G. "Future Options for the Management of Hepatitis C", Seminars in Liver Disease, vol. 19, Supp. 1 (1999), pp. 103-112.
Dixon, S. M., "A Spiroisoazolinoproline-based Amino Acid Scaffold for Solid Phase and One-Bead—One-Compound Library Synthesis" Journal of Combinatorial Chemistry, 9 (2007) pp. 143-157.
Dunsdon, R., "Solid Phase Synthesis of Aminoboronic Acids: Potent Inhibitors of the Hepatitis C Virus NS3 Proteinase", Bioorganic & Medicinal Chemistry Letters, 10 (2000), pp. 1577-1579.
Elemes, "Synthesis of enantiopure a-deuterated Boc-L amino acids," J. Chemical Society, Perkin Trans. vol. 1 (1995) pp. 537-540.
Esch, P.M., "Reductive Cyclization of Carbon-Centered Glycine Radicals; A Novel Synthetic route to Cyclic a-Amino Acids", Tetrahedron, vol. 48, No. 22 (1992), pp. 4659-4676.

Farmer, L., "Inhibitors of Hepatitis C Virus NS3-4A Protease: P2 Proline Variants," Letters In Drug Design and Discovery (2005), 2, pp. 497-502.

Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.

Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.

Gallagher, D., "Complex-Induced Proximity Effects: Evidence for a Prelithiation Complex and a Rate-Determining Deprotonation in the Asymmetric Lithiation of Boc-Pyrrolidine by an i-PrLi/(−) Sparteine Complex", J. Org. Chem., vol. 60 (1995), pp. 7092-7093.

Gallagher, D., "Chiral Organolithium Complexes: The Effect of Ligand Structure on the Enantioselective Deprotonation of Boc-Pyrrolidine", J. Org. Chem., vol. 60 (1995), pp. 8148-8154.

Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(1 H-Imidazol-1-yl)benzoyl]-7-isopropyl-3,7-diazabicyclo[3.3.1]nonane Dihydroperchlorate", J. Med. Chem, vol. 39, No. 13 (1996), pp. 2559-2570.

Golina, S., "Vulcanisation of Poly(diethyl-n-butylamino) Phosphazenes", Internay'l. Polymer Science & Tech., vol. 18, No. 3 (1991), pp. T20-T22.

Han, W., "a-Ketoamides, a-Ketoesters and a-Diketones as HCV NS3 Protease Inhibitors", Bioorganic & Medicinal Chemistry Letters 10 (2000), pp. 711-713.

Hofma, S.H. "Recent developments in Coated Stents," Curr. Interventional Cardiology Reports, 3 (2001), pp. 28-36.

Janssen, H.L.A., "Suicide Associated with a-Interferon Therapy for Chronic Viral Hepatitis", J. Hepatal., 21 (1994), pp. 241-243.

Johansson, A., "Acyl Sulfonamides as Potent Protease Inhibitors of the Hepatitis C Virus Full-Length NS3 (Protease-Helicase/NTPase): A comparative Study of Different C-Terminals", Bioorganic & Medicinal Chemistry, 11 (2003), pp. 2551-2568.

Johansson, P., "Potent inhibitors of the hepatitis C virus NS3 protease: Use of a novel P2 cyclopentane-derived template," Bioorganic & Medicinal Chemistry (2006), 14, pp. 5136-5151.

Kakei, H., "Catalytic Asymmetric Epoxidation of a, β-Unsaturated Esters Using an Yttrium-Biphenyldiol Complex", J. Am. Chem. Soc., vol. 127 (2005), pp. 8962-8963.

Kalkeri, G., "Expression of HCV Protease in the Liver of Mice Results in Liver Injury Which can be Inhibited by VX-950, A Vertex HCV Protease Inhibitor," AALSD Abstracts, Hepatology (2004), 40(4), pp. 281A.

Kamandi, E., "Die Synthese von β-Phenyl-Isoserinen Durch Ammonolyse von β-Phenyl-Glycidestem, I", Archiv de Pharmazie, vol. 307 No. 11 (1974), pp. 871-878.

Kao, J.H., "Efficacy of Consensus Interferon in the Treatment of Chronic Hepatitis", J. Gastroenterol. Hepatol, 15 (2000), pp. 1418-1423.

Kerrick, S., "Asymmetric Deprotonations: Enantioselective Syntheses of 2-Substituted (tert-Butoxycarbonyl) pyrrolldines", J. Amer. Chem. Soc., vol. 113 (1991), pp. 9708-9710.

Kieffer, T., "Genetic Heterogeneity in the HCV NS3 Protease of Untreated Genotype 1 Patients has Little Effect on the Sensitivity to VX-950", Hepatol, vol. 42 (2005), p. 537A.

Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.

Kieffer, T., "Combination of Telaprevir (VX-950) and Peg-lfn-Alfa Suppresses both Wild-Type Virus and Resistance Variants in HCV Genotype 1-Infected Patients in a 14-Day Phase 18 Study", Hepatol. 44, Supp.2 (2006), p. 222A.

Kieffer, Genetic Heterogeneity in the HCV Ns3 Protease of Untreated Genotype 1 Patients Has Little Effect on the Sensitivity of the VX-950, 12th Internat'l Conf. on Hep. C Virus and Related Viruses, Montreal, Canada, Oct. 2-6, 2005.

Kim, J., "Hepatitis C Virus NS3 RNA Helicase Domain with a bound Oligonudeotide: The Crystal Structure Provides Insights into the Mode of Unwinding", Structure, vol. 6, No. 1, (1998), pp. 89-100.

Kim, J., "Crystal structure of the hepatitis C virus NS3 protease domain complexed with a synthetic NS4A cofactor peptide," Cell, vol. 87 (1996), pp. 343-355; [and Kim, J. "Erratum," Cell, vol. 89, No. 1 (1997), p. 159].

Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.

Kwong, A.D., "Structure and Function of Hepatitis C Virus NS3 Helicase", Top Microbiol. Immunol., vol. 242, (2000), pp. 171-196.

Kwong, A.D., "Hepatitis C Virus NS3/4A Protease", Antiviral Res., vol. 40 (1998), pp. 1-18.

Kwong, A.D., "Erratum: Hepatitis C Virus NS3/4A Protease", Antiviral Res., vol. 41 (1999), pp. 65-84 C.

Kwong, A.D., "An Orally Bioavailable Inhibitor of the HCV NS3-4a Protease; a Potential HCV Therapeutic", 5th Antivir. Drug Disc. and Devel. Summit, (Mar. 30, 2004).

Kwong, A.D., "HCV Protease Inhibitors: Activity and Resistance," 13th Conference on Retroviruses and Opp. Infections (CROI), Denver, CO, Feb. 5-8, 2006.

Kwong, A.D., "Beyond Interferon and Ribavirin: Antiviral Therapies for Hepatitis C Virus", Drug Disc. Today: Ther. Strategies, vol. 3 (2006), pp. 211-220.

Kwong, A.D., "VX-950: A Novel Hepatitis C Protease Inhibitor", HepDART (2005).

Lamar, J., "Novel P4 Truncated Tripeptidyl a-ketoamides as HCV Protease Inhibitors", Bio. & Med. Chem. Let, vol. 14 No. 1 (2004), pp. 263-266.

Landro, J.A. "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 36 (1997) pp. 9340-9348.

Laplante, S., "NMR Line-Broadening and Transferred Noesy as a Medicinal Chemistry Tool for Studying Inhibitors of the Hepatitis C Virus NS3 Protease Domain", Bioorganic & Medicinal Chemistry Letters, 10 (2000), pp. 2271-2274.

Lavanchy, D., "Global Surveillance and control of Hepatitis C", J. Viral Hepatitis, 6 (1999), pp. 35-47.

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Internat'l Symposium on Viral Hep. and Liver Dis., (2006).

Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol., vol. 131, No. 3 (2006), pp. 950-951.

Lehmann, Über die chemischen and biologischen Eigenschaften einiger a-Aminoketone, Helvetica Chimica Acta., vol. 33 (1950), pp. 1217-1226.

Lin, C., "Structure-Based Mutagenesis Study of Hepatitis C Virus NS3 Helicase", J. Virol., vol. 73, No. 10 (1999), pp. 8798-8807.

Lin, K., "Combination of a Hepatitis C Virus NS3-NS4A Protease Inhibitor and a Interferon Synergistically Inhibits Viral RNA Replication and Facilitates Viral RNA Clearance in Replicon Cells", Antimicrob. Agents Chemo, vol. 48 (2004), pp. 4784-4792.

Lin, K., "VX-950, a Novel Hepatitis C Virus (HCV) NS3-4A Protease Inhibitor, Exhibits Potent Antiviral Activities in HCV Replicon Cells", Antimicrob. Agents Chemo, vol. 50, No. 5 (2006), pp. 1813-1822.

Lin, K., "VX-950: A Tight-Binding HCV Protease Inhibitor with a Superior Sustained Inhibitory Response in HCV Replicon Cells", Hepatol, vol. 38 (2003), p. 222A.

Lin, C., "Discovery and Development of VX-950, a Novel, Covalent and Reversible Inhibitor of Hepatitis C Virus NS3-4A Serine Protease", Infect. Disord. Drug Targets, vol. 6, No. 1 (2006), pp. 3-16.

Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.

Llinas-Brunet, M., "Highly Potent and Selective Peptide-Based Inhibitors of the Hepatitis C Virus Serine Protease: Towards Smaller Inhibitors", Bioorganic & Medicinal Chemistry Letters, 10 (2000), pp. 2267-2270.

Llinas-Brunet, M., "Peptide-Based Inhibitors of the Hepatitis C Virus Serine Protease", Bioorganic & Medicinal Chemistry Letters, 8 (1998), pp. 1713-1718.

Llinas-Brunet, M., "Studies on the C-Terminal of Hexapeptide Inhibitors of the Hepatitis C virus Serine Protease", Bioorganic & Medicinal Chemistry Letters, 8 (1998), pp. 2719-2724.

Lohmann, F. "Replication of Subgenomic Hepatitis C Virus RNAs in a Hepatoma Cell Line", Science, 285.5454 (1999) p. 110.

Marigo, M., "Asymmetric Organocatalytic Epoxidation of a,β-Unsaturated Aldehydes with Hydrogen Peroxide", J. Am. Chem. Soc., vol. 127, No. 19 (2005), pp. 6964-6965.

Markland, W., "Broad-Spectrum Antiviral Activity of the IMP Dehydrogenase Inhibitor VX-497: a Comparison with Ribavirin and Demonstration of Antiviral Additivity with Alpha Interferon", Antimicrob. Ag. Chem., vol. 44, No. 4 (2000), pp. 859-866.

McLaren, R., "Infrared Observations of Circumstellar Ammonia in OH/IR Supergiants," Astrophysical Journal (1980), 240(3, Pt. 2), pp. L159-L163.

Mehdi, The Inhibition of Human Neutrophil Elastase and Cathepsin G by Peptidyl 1,2-Dicarbonyl Derivatives, Biochem & Biophys. Res. Comm., vol. 166, No. 2 (1990), pp. 595-660.

Monn, J., "A Concise, Stereocontrolled Thiazolium Ylide Approach to Kainic Acid", J. Organic Chem., vol. 59, No. 10 (1994), pp. 2773-2778.

Moradpour, D., "Current and Evolving Therapies for Hepatitis C", Eur. J. Gastroenterol. Hepatol., vol. 11 (1999), pp. 1199-1202.

Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Virol., vol. 71, No. 5 (1997), pp. 3767-3775.

Newman, A., "Solid-state Analysis of the Active Pharmaceutical Ingredient in Drug Products", vol. 8, No. 19 (2003), pp. 898-905.

Patent Abstracts of Japan, vol. 1997, No. 9, Sep. 30, 1997.

Perni, R., "NS3-4A Protease as a Target for Interfering with Hepatitis C Virus Replication", Drug News Perspect., vol. 13, No. 2 (2000), pp. 69-77.

Perni, R.B., "Inhibitors of Hepatitis C Virus NS3-4A Protease 1. Non-Charged Tetrapeptide Variants", Bioorganic & Medicinal Chemistry Letters, 13 (2003), pp. 4059-4063.

Perni, R.B., "Inhibitors of Hepatitis C Virus NS3-4A Protease 2. Warhead SAR and Optimization", Bioorganic & Medicinal Chemistry Letters, 14 (2004), pp. 1441-1446.

Perni, R.B., "Inhibitors of Hepatitis C Virus NS3-4A Part 3: P2 Proline Variants", Bioorganic & Medicinal Chemistry Letters, 14 (2004), pp. 1939-1942.

Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.

Perni, R. "VX-950: The Discovery of an Inhibitor of the Hepatitis C NS3-4A Protease and a Potential Hepatitis C Virus Therapeutic", Hepatology, vol. 38 (2003) p. 624A.

Perni, R., "Toward Smaller HCV NW-4A Protease Inhibitors: 3-Substituted Proline-based Tripeptide Scaffolds," Abstracts of Papers, 229th ACS National Meeting, San Diego, CA, United States, Mar. 13-17, 2005, MEDI-350.

Perni, R., "The Design of Inhibitors of the HCV NS3-4A Protease: The Identification of a Clinical Development Candidate, VX-950," ACS National Medicinal Chemistry Symposium, Madison, WI, Jun. 2004.

Perni, R., "Inhibitors of Hepatitis C Virus NS3-4A Protease. Effect of P4 Capping Groups on Inhibitory Potency and Pharmacokinetics," Bioorganic & Medicinal Chemistry Letters (2007), 17(12), pp. 3406-3411.

Perni, R., "Properties and Preclinical Profile of VX-950, An Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.

Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.

Pippel, D., "Complex-Induced Proximity Effects: Steroselective Carbon-Carbon Bond Formation in Chiral Auxiliary Mediated β-Lithiation-Substitution Sequences of β-Substituted Secondary Carboxamides", J. Org. Chem., vol. 63 (1998), pp. 2-3.

Poliakov, A. "Structure-Activity Relationships for the Selectivity of Hepatitis C Virus NS3 Protease Inhibitors", Biochimica et Biophysica Acta, 1672 (2004), pp. 51-59.

Ramachandran, R., "Anti-Viral Activity of VX-950 Resolves Expression of an HCV-Associated Gene Signature", J. Hepatol, vol. 44, Supp. 2 (2006), p. S223.

Reesink, H., "Initial Results of a Phase 1B, Multiple-Dose Study of VX-950, a Hepatitis C Virus Protease Inhibitor", Gastroent., vol. 128, No. 4, Supp. 2 (2005), pp. A696-A697.

Reesink, H., "Rapid Decline of Viral RNA in Hepatitis C Patients Treated with VX-950: A Phase 1b, Placebo-Controlled Randomized Study", Gastroenterol., vol. 131, No. 4 (2006), pp. 997-1002.

Reesink, H., "Final Results of a Phase 1B, Multiple-Dose Study of VX-950, a Hepatitis C Virus Protease Inhibitor", Hepatology, vol. 42, No. 4, Supp. 1 (2005), pp. 234A-235A.

Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.

Renault, P.F., "Side Effects of Alpha Interferon", Seminars in Liver disease, 9 (1989), pp. 273-277.

Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.

Sagnard, I., "Enantioselective Synthesis of Cyclopropane a-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-3152.

Schneider, F. "Enhanced Plasma Concentration by Selective Deuteration of Rofecoxib in Rats," Arzneimittel-Forschung (Drug. Res.) vol. 56 (4) (2006), pp. 295-300.

Schneider, F. "Changed Phosphodiestarase Selectivity and Enhanced in vitro Efficacy by Selective Deuteraton of Sildenafil," Arzneimittel-Forschung (Drug. Res.) vol. 57 (6) (2007), pp. 293-298.

Taber, D., "Asymmetric Nucleophilic Epoxidation", Org. Chem. Highlights, (2004).

Takamizawa, A., "Structure and Organization of the Hepatitis C Virus Genome Isolated from Human Carriers", J. Virol., 65 (1991), pp. 1105-1113.

Taliani, M., "A continuous Assay of Hepatitis C Virus Protease Based on Resonance Energy Transfer Depsipeptide Substrates", Anal. Biochem., vol. 240 (1996), pp. 60-67.

Tan, S., "Strategies for Hepatitis C Therapeutic Intervention: Now and Next", Current Op. in Pharmacology, vol. 4, No. 5 (2004), pp. 465-470.

Tazulakhova, E.B., "Russian Experience in Screening, Analysis and Clinical Application of Novel Interferon Inducers", J. Interferon Cytokine Res., 21 (2001), pp. 65-73.

Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.

Toom, L., "Microwave-Assisted Raney Nickel Reduction of Bispidinone Thioketals to N,N'-Dialkylbispidines", Synthesis, vol. 12 (2006), pp. 2064-2068.

Trask, A.V., "Solvent-drop grinding: green polymorph control of cocrystallisation", Chemical Communications, (2004), pp. 890-891.

Udding, J.H., "Transition Metal-Catalyzed Chlorine Transfer Cyclizations of Carbon-Centered Glycine Radicals; A Novel Synthetic Route to Cyclic a-Amino Acids", Tetrahedron, vol. 50, No. 6 (1994), pp. 1907-1918.

Victor, F., "P1 and P3 optimization of novel bicycloproline P2 bearing tetrapeptidyl a-ketoamide based HCV protease inhibitors", Biorganic & Medicinal Chemistry Letters, 14 (2004), pp. 257-261.

Vishweshwar, P., "Pharmaceutical Co-Crystals", J. Pharm. Sci., vol. 95, No. 3 (2006), pp. 499-516.

Walker, M.A., "Hepatitis C Virus: An Overview of Current Approaches and Progress", DDT, 4 (1999), pp. 518-529.

Wang, Z., "Asymmetric Epoxidation of trans-β-Methylstyrene and 1-Phenylcyclohexene Using a D-Fructose-Derived Ketone: (R,R)- trans-β-Methylstyrene Oxide and (R,R)-1-Phenylcyclohexene Oxide", Org. Syntheses, vol. 80 (2003), pp. 9-13.

Weiland, O., "Interferon Therapy in Chronic Hepatitis C Virus Infection", FEMS Microiol. Rev., 14 (1994), pp. 279-288.

Weissbuch, I. et al. "Understanding and control of nucleation, growth, habit, dissolution and structure of two- and three-dimensional crystals using 'tailor-made' auxiliaries," Acta Crystallographica B vol. B51 (1995), pp. 115-148.

White, P.W. "Blunting the Swiss Army Knife of Hepatitis C Virus: Inhibitors of NS3/4A Protease" Progress in Medicinal Chemistry 44 (2006), pp. 65-107.

Yao, N., N. "Molecular views of viral polyprotein processing revealed by the crystal structure of the hepatitis C virus bifunctional protease-helicase," Structure (1999), 7, pp. 1353-1363.

Yasuda, M., "Synthesis of Conformationally Defined Glutamic Acid Analogues from Readily Available Diels-Alder Adducts", Chem. And Pharm. Bulletin (1995), pp. 1318-1324.

Yip, Y. Discovery of a Novel Bicycloproline P2 Bearing Peptidyl a-Ketoamide LY514962 as HCV Protease Inhibitor, Bio. & Med. Chem. Let., vol. 14, No. 1 (2004), pp. 251-256.

Yip, Y., "P4 and P1' Optimization of Bicycloproline P2 Bearing Tetrapeptidyl a-Ketoamides as HCV Protease Inhibitors", Bio. & Med. Chem. Let., vol. 14, No. 9 (2004), pp. 5007-5011.

Yun, C. "Oxidation of the antihistaminic drug terfenadine in human liver microsomes: Role of Cytochrome P-450 3A(4) in N-dealkylation and C-hydroxylation", Drug metabolism and Disposition, 21(3) (1993) pp. 403-409.

ISR dated Jul. 23, 2007 from PCT/US2007/006320.
ISR dated Aug. 3, 2007 from PCT/US2007/004995.
ISR dated Nov. 16, 2007 from PCT/US2007/64294.
ISR dated Dec. 27, 2007 from PCT/US2006/032481.
ISR dated Sep. 5, 2008 from PCT/US2008/002568.
ISR dated Jan. 21, 2009 from PCT/US2008/010254.
ISR dated Jan. 23, 2009 from PCT/US2008/002395.

CO-CRYSTALS AND PHARMACEUTICAL COMPOSITIONS COMPRISING THE SAME

CROSS-REFERENCE

This application is a divisional of U.S. Ser. No. 11/711,213, filed Feb. 27, 2007 now U.S. Pat. No. 8,039,475, and also claims the benefit under 35 U.S.C. §119 of U.S. Application Ser. No. 60/777,221, filed Feb. 27, 2006. Both of these applications are incorporated herein in their entirety.

BACKGROUND OF THE INVENTION

Infection by hepatitis C virus ("HCV") is a compelling human medical problem. HCV is recognized as the causative agent for most cases of non-A, non-B hepatitis, with an estimated human prevalence of 3% globally [A. Alberti et al., "Natural History of Hepatitis C," *J. Hepatology*, 31 (Suppl. 1), pp. 17-24 (1999)]. Nearly four million individuals may be infected in the United States alone [M. J. Alter et al., "The Epidemiology of Viral Hepatitis in the United States," *Gastroenterol. Clin. North Am.*, 23, pp. 437-455 (1994); M. J. Alter "Hepatitis C Virus Infection in the United States," *J. Hepatology*, 31 (Suppl. 1), pp. 88-91 (1999)].

Upon first exposure to HCV, only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," *FEMS Microbiology Reviews*, 14, pp. 201-204 (1994); D. Lavanchy, "Global Surveillance and Control of Hepatitis C," *J. Viral Hepatitis*, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", *FEMS Microbiology Reviews*, 14, pp. 211-220 (1994); I. Saito et al., "Hepatitis C Virus Infection is Associated with the Development of Hepatocellular Carcinoma," *Proc. Natl. Acad. Sci. USA*, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et al., "Genetic Organization and Diversity of the Hepatitis C Virus." *Proc. Natl. Acad. Sci. USA*, 88, pp. 2451-2455 (1991); N. Kato et al., "Molecular Cloning of the Human Hepatitis C Virus Genome From Japanese Patients with Non-A, Non-B Hepatitis," *Proc. Natl. Acad. Sci. USA*, 87, pp. 9524-9528 (1990); A. Takamizawa et al., "Structure and Organization of the Hepatitis C Virus Genome Isolated From Human Carriers," *J. Virol.*, 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et al., "Nonstructural Protein 3 of the Hepatitis C Virus Encodes a Serine-Type Proteinase Required for Cleavage at the NS3/4 and NS4/5 Junctions," *J. Virol.*, 67, pp. 3835-3844 (1993); A. Grakoui et al., "Characterization of the Hepatitis C Virus-Encoded Serine Proteinase: Determination of Proteinase-Dependent Polyprotein Cleavage Sites," *J. Virol.*, 67, pp. 2832-2843 (1993); A. Grakoui et al., "Expression and Identification of Hepatitis C Virus Polyprotein Cleavage Products," *J. Virol.*, 67, pp. 1385-1395 (1993); L. Tomei et al., "NS3 is a serine protease required for processing of hepatitis C virus polyprotein", *J. Virol.*, 67, pp. 4017-4026 (1993)].

The HCV NS protein 3 (NS3) is essential for viral replication and infectivity [Kolykhalov, *J. Virology*, Volume 74, pp. 2046-2051 2000 "Mutations at the HCV NS3 Serine Protease Catalytic Triad abolish infectivity of HCV RNA in Chimpanzees]. It is known that mutations in the yellow fever virus NS3 protease decrease viral infectivity [Chambers, T. J. et al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147-8157 (1994)].

The HCV NS3 serine protease and its associated cofactor, NS4A, help process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently, HCV NS3 serine protease is also an attractive target for drug discovery.

Until recently, the only established therapy for HCV disease was interferon treatment. However, interferons have significant side effects [M. A. Wlaker et al., "Hepatitis C Virus: An Overview of Current Approaches and Progress," *DDT*, 4, pp. 518-29 (1999); D. Moradpour et al., "Current and Evolving Therapies for Hepatitis C," *Eur. J. Gastroenterol. Hepatol.*, 11, pp. 1199-1202 (1999); H. L. A. Janssen et al. "Suicide Associated with Alfa-Interferon Therapy for Chronic Viral Hepatitis," *J. Hepatol.*, 21, pp. 241-243 (1994); P. F. Renault et al., "Side Effects of Alpha Interferon," *Seminars in Liver Disease*, 9, pp. 273-277 (1989)] and induce long term remission in only a fraction (~25%) of cases [O. Weiland, "Interferon Therapy in Chronic Hepatitis C Virus Infection", *FEMS Microbiol. Rev.*, 14, pp. 279-288 (1994)]. Recent introductions of the pegylated forms of interferon (PEG-INTRON® and PEGASYS®) and the combination therapy of ribavirin and interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

VX-950, an HCV inhibitor with its structure shown below is such a compound in need. VX-950 is described in PCT Publication Number WO 02/18369, which is incorporated herein by reference in its entirety.

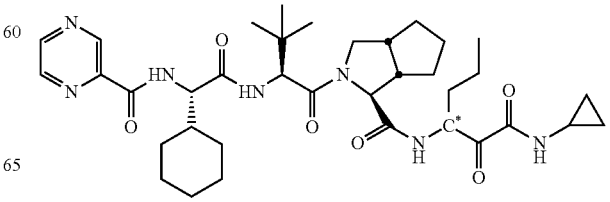

SUMMARY OF THE INVENTION

In general, the present invention relates to compositions containing the HCV inhibitor VX-950 and a specific co-crystal former (CCF). Under certain circumstances, VX-950 and the CCF together may form a crystalline composition, i.e., co-crystal. Compared to their free forms, specific VX-950 co-crystals are advantageous as they possess improved dissolution, higher aqueous solubility, and greater solid state physical stability than amorphous VX-950 dispersions. The specific VX-950 co-crystals provide a reduced mass of the dosage form and therefore lower pill burden since the VX-950 co-crystals also exhibit higher bulk densities relative to amorphous forms. Further, VX-950 co-crystals provide manufacturing advantages relative to amorphous forms which require spray drying, melt extrusion, lyophilization, or precipitation.

In one aspect, the compositions provided by this invention each contain VX-950 and a CCF compound selected from the group consisting of salicylic acid (SA), 4-amino salicylic acid (4-ASA), and oxalic acid (OA), as a CCF. In one embodiment, VX-950 and the CCF together are in the crystalline form in the composition.

In another aspect, this invention provides three VX-950 co-crystals each of which includes VX-950 and a CCF. Specifically, the first co-crystal includes VX-950 and salicylic acid (SA) as the CCF. In some embodiments, when the CCF is SA, the X-ray power diffraction (XRPD) spectrum of the co-crystal exhibits peaks at about 4.43, 7.63, 8.53, 9.63, 12.89, 14.83 and 16.29 2-Theta; and its differential scanning calorimetry (DSC) thermogram shows melting points at about 137° C. and about 223° C. The second co-crystal includes VX-950 and 4-amino salicylic acid (4-ASA) as the CCF. In some embodiments, when the CCF is 4-ASA, the XRPD spectrum of the co-crystal exhibits peaks at about 4.37, 7.57, 8.47, 9.59, 12.81, and 14.75 2-Theta; and its DSC thermogram shows a melting point at about 177° C. The third co-crystal includes VX-950 and oxalic acid (OA) as the CCF. In some embodiments, when the CCF is OA, the XRPD spectrum of this co-crystal exhibits peaks at about 4.65, 6.17, 9.63, 12.65, 14.91, and 28.97 2-Theta. In some embodiments, the ratio of the number of molecules of VX-950 and the CCF in the unit cell are between 0.2 and 5 (e.g., 1). In some embodiments, VX-950 and the CCF are both in the solid state (e.g., crystalline) and are bonded non-covalently (i.e., by hydrogen bond).

In another aspect, the invention provides co-crystals of the formula $(VX-950)_m:(CCF)_n$, wherein CCF is a co-crystal former selected from the group consisting of salicylic acid, 4-amino salicylic acid, and oxalic acid; and m and n, independently, are an integer of 1 to 5. In some embodiments, m and n are both 1.

In another aspect, the invention provides a co-crystal of VX-950 and a CCF, wherein the CCF is a solid at the room temperature, and VX-950 and the CCF interact by non-covalent bonds. In some embodiments, the CCF is selected from the group consisting of salicylic acid, 4-amino salicylic acid, and oxalic acid. In certain embodiments, the non-covalent bond interactions between VX-950 and the CCF include hydrogen bonding and van der Waals interactions.

In still another aspect, this invention provides a pharmaceutical composition that includes one of the three VX-950 co-crystals described above. In one embodiment, the pharmaceutical composition further includes a diluent, solvent, excipient, or carrier.

Still another aspect of this invention provides a method of making a co-crystal of VX-950 and a CCF selected from the group consisting of salicylic acid, 4-amino salicylic acid, and oxalic acid. The method includes the steps of providing VX-950; providing the co-crystal former salicylic acid, 4-amino salicylic acid, or oxalic acid; grinding, heating, co-subliming, co-melting, or contacting in solution VX-950 with the co-crystal former under crystallization condition so as to form the co-crystal in solid phase; and then optionally isolating the co-crystal formed thereby. In some embodiments, the making a co-crystal of VX-950 and a CCF includes providing VX-950 and the CCF in a molar ratio between about 10 to about 0.1.

In yet another aspect, the invention provides a method for modulating a chemical or physical property of interest (such as melting point, solubility, dissolution, hygroscopicity, and bioavailability) of a co-crystal containing VX-950 and a CCF selected from the group consisting of salicylic acid, 4-amino salicylic acid, and oxalic acid. The method includes the steps of measuring the chemical or physical property of interest for VX-950 and the co-crystal former; determining the mole fraction of the VX-950 and the co-crystal former that will result in the desired modulation of the chemical or physical property of interest; and preparing the co-crystal with the molar fraction as determined.

The compositions and co-crystals of this invention can be used for treating diseases implicated by or associated with HCV. Thus, also within the scope of this invention is a method of treating such diseases, which comprising administering to a subject in need thereof a therapeutically effective amount of a co-crystal of this invention or a composition of this invention.

The compositions and co-crystals of this invention can also be used as seeds to prepare additional co-crystals containing an active ingredient that can be the same as or different from VX-950, and a CCF that can also be the same as or different from salicylic acid, 4-amino salicylic acid, and oxalic acid. For instance, a small amount of a co-crystal of this invention can be placed into a solution containing the desired active ingredient and the CCF and the mixture is allowed to sit so that additional co-crystal can be formed with and grown out of the existing co-crystal.

Additionally, the compositions and co-crystals of this invention can be used as research tools. For instance, crystal structures of the co-crystals can be used for molecular modeling to identify other possible co-crystal formers. They can be used to study the pharmacological properties (such as bioavailability, metabolism, and efficacy).

DETAILED DESCRIPTION OF THE INVENTION

Figure 1:
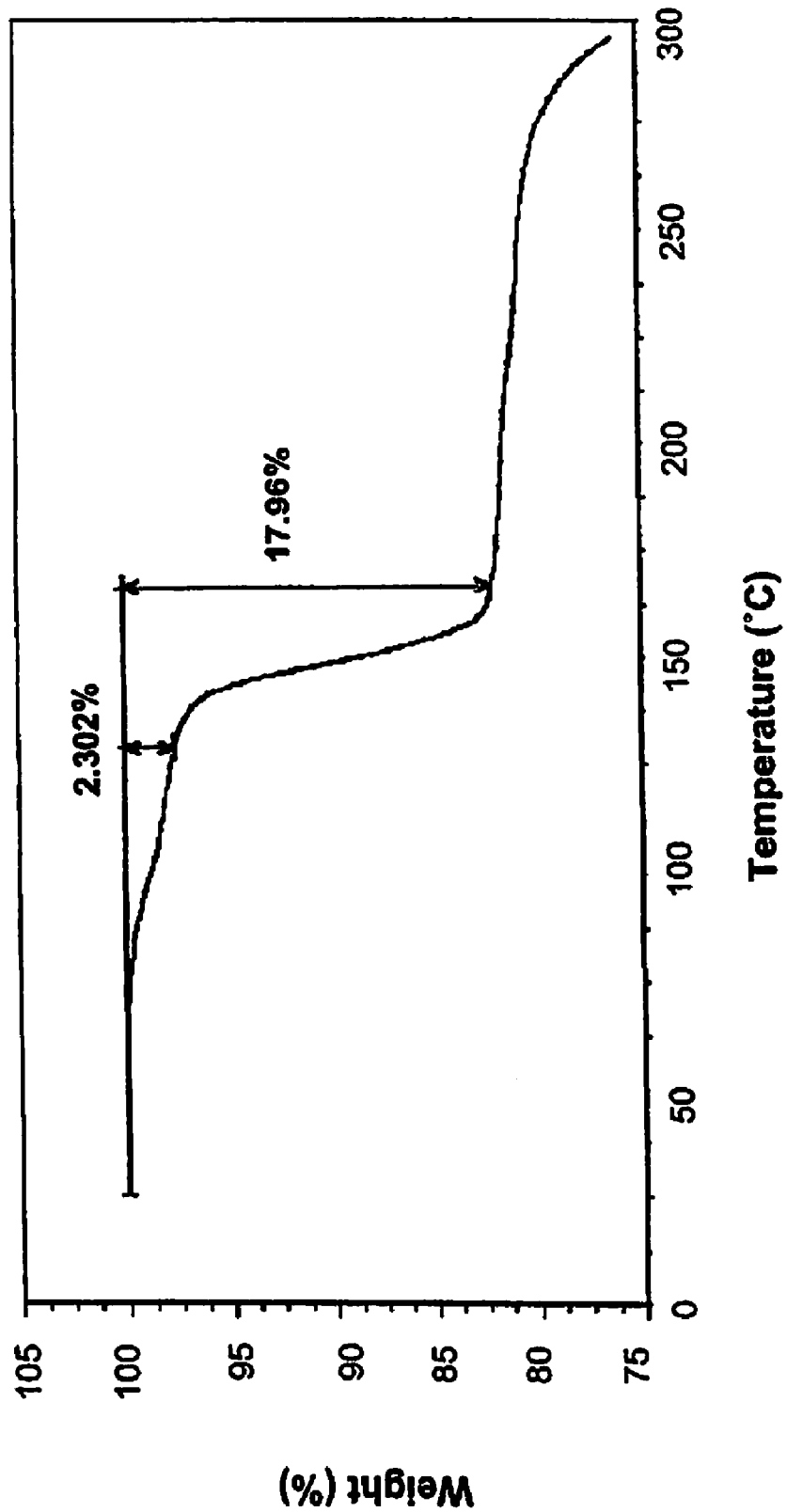
FIG. 1 shows a thermogravimetric analysis (TGA) spectrum of the co-crystal of VX-950 and SA.

Methods for preparing and characterizing a co-crystal are well documented in the literature. See, e.g., Trask et al., Chem. Commun., 2004, 890-891; and O. Almarsson and M. J. Zaworotko, Chem. Commun., 2004, 1889-1896. These methods in general are also suitable for preparing and characterizing co-crystals of this invention.

Examples of preparing co-crystals with an active pharmaceutical ingredients and a CCF include ball-milling, melting in a reaction block, evaporating solvent, slurry conversion, blending, sublimation, or modeling. In the ball-milling method, certain molar ratios of the components of the co-crystal (e.g., a compound of interest, such as VX-950 in this invention, and a CCF) are mixed and milled with balls. Optionally, a solvent such as methyl ethyl ketone can be added to the mixture being ball milled After milling, the mixture can be dried under vacuum either at the room temperature or in the heated condition, which typically gives a powder product. In the melting method, the components of a co-crystal (e.g., a CCF and VX-950) are mixed, optionally with a solvent such as acetonitrile. The mixture is then placed in a reaction block with the lid closed, and then heated to the endotherm. The resulting mixture is then cooled off and solvent, if used, removed. In the solvent-evaporation method, each component of a co-crystal is first dissolved in a solvent (or a solvent mixture, such as 50/50 toluene and acetonitrile), and the solutions are then mixed together. The mixture is then allowed to sit and solvent to evaporate to dryness, to yield the co-crystal.

Examples of characterization methods include thermogravimetric analysis (TGA), differential scanning calorimetry (DSC), X-ray powder diffraction (XRPD), solubility analyses, dynamic vapor sorption, infrared off-gas analysis, and suspension stability. TGA can be used to investigate the presence of residual solvents in a co-crystal sample, and to identify the temperature at which decomposition of each co-crystal sample occurs. DSC can be used to look for thermo-transitions occurring in a co-crystal sample as a function of temperature and determine the melting point of each co-crystal sample. XRPD can be used for structural characterization of the co-crystal. Solubility analysis can be performed to reflect the changes in the physical state of each co-crystal sample. And suspension stability analysis can be used to determine the chemical stability of a co-crystal sample in a solvent.

An effective amount of co-crystals or compositions of this invention, each including VX-950 and a co-crystal former (CCF) selected from the group consisting of salicylic acid, 4-amino salicylic acid, and oxalic acid, can be used to treat diseases implicated or associated with the HCV. An effective amount is the amount which is required to confer a therapeutic effect on the treated subject, e.g. a patient. The effective amount of a co-crystal of VX-950 and the CCF is between about 0.1 mg/kg to about 150 mg/kg (e.g., from about 1 mg/kg to about 60 mg/kg). Effective doses will also vary, as recognized by those skilled in the art, dependent on route of administration, excipient usage, and the possibility of co-usage with other therapeutic treatments including use of other therapeutic agents and/or therapy.

The co-crystals or pharmaceutical compositions of this invention can be administered to the subject in need thereof (e.g., cells, a tissue, or a patient (including an animal or a human)) by any method that permits the delivery of the compound VX-950, e.g., orally, intravenously, or parenterally. For instance, they can be administered via pills, tablets, capsules, aerosols, suppositories, liquid formulations for ingestion or injection or for use as eye or ear drops, dietary supplements, and topical preparations.

The pharmaceutical compositions can include diluents, solvents, excipients and carriers such as water, Ringer's solution, isotonic saline, 5% glucose, and isotonic sodium chloride solution. In another embodiment, the pharmaceutical composition can further include a solubilizing agent such as cyclodextrin. Additional examples of suitable diluents, solvents, excipients, carriers, and solubilizing agents can be found, e.g., in U.S. Pharmacopeia 23/National Formulary 18, Rockville, Md., U.S. Pharmacopeia Convention, Inc., (1995); Ansel H C, Popovich N G, Allen Jr L V. Pharmaceutical Dosage Forms and Drug Delivery Systems, Baltimore Md., Williams & Wilkins, (1995); Gennaro A R., Remingtons: The Science and Practice of Pharmacy, Easton Pa., Mack Publishing Co., (1995); Wade A, Weller P J. Handbook of Pharmaceutical Excipients, 2nd Ed, Washington D.C., American Pharmaceutical Association, (1994); Baner G S, Rhodes C T. Modern Pharmaceutics, 3rd Ed., New York, Marcel Dekker, Inc., (1995); Ranade V V, Hollinger M A. Drug Delivery Systems. Boca Raton, CRC Press, (1996).

The pharmaceutical compositions can also include aqueous solutions of the co-crystal, in an isotonic saline, 5% glucose or other well-known pharmaceutically acceptable excipient(s). Solubilizing agents such as cyclodextrins, or other solubilizing agents well-known to those familiar with the art, can be utilized as pharmaceutical excipients for delivery of the therapeutic compound VX-950. As to route of administration, the co-crystals or pharmaceutical compositions can be administered orally, intranasally, transdermally, intradermally, vaginally, intraaurally, intraocularly, buccally, rectally, transmucosally, or via inhalation, or intravenous administration. The compositions may be delivered intravenously via a balloon catheter. The compositions can be administered to an animal (e.g., a mammal such as a human, non-human primate, horse, dog, cow, pig, sheep, goat, cat, mouse, rat, guinea pig, rabbit, hamster, gerbil, ferret, lizard, reptile, or bird).

The co-crystals or pharmaceutical compositions of this invention also can be delivered by implantation (e.g., surgically) such with an implantable device. Examples of implantable devices include, but are not limited to, stents, delivery pumps, vascular filters, and implantable control release compositions. Any implantable device can be used to deliver the compound VX-950 as the active ingredient in the co-crystals or pharmaceutical compositions of this invention, provided that 1) the device, compound VX-950 and any pharmaceutical composition including the compound are biocompatible, and 2) that the device can deliver or release an effective amount of the compound to confer a therapeutic effect on the treated patient.

Delivery of therapeutic agents via stents, delivery pumps (e g, mini-osmotic pumps), and other implantable devices is known in the art. See, e.g., "Recent Developments in Coated Stents" by Hofma et al., published in *Current Interventional Cardiology Reports,* 2001, 3: 28-36, the entire contents of which, including references cited therein, are incorporated herein. Other descriptions of implantable devices, such as stents, can be found in U.S. Pat. Nos. 6,569,195 and 6,322,847, and PCT International Publication Numbers WO 04/0044405, WO 04/0018228, WO 03/0229390, WO 03/0228346, WO 03/0225450, WO 03/0216699, and WO 03/0204168, each of which (as well as other publications cited herein) is incorporated herein in its entirety.

Described below are examples of preparing and characterizing co-crystals of this invention, which are meant to be only illustrative and not to be limiting in any way.

EXAMPLE 1

Preparation by Ball-Milling Method

Salicylic Acid (SA): 70 mg of VX-950 and an equal molar equivalent of SA (Sigma Chemicals Co., St. Louis, Mo., USA) as the CCF were mixed with 50 μL of methyl ethyl ketone ("MEK"). The components were milled using a Wig-L-Bug apparatus for 10 minutes. After milling, a batch was dried in a vacuum oven at 75° C. for 2 hours. The resulting material was off-white in color.

4-Amino Salicylic Acid (4-ASA): 70 mg of VX-950 and an equal molar equivalent of 4-ASA (15.8 mg) (Sigma Chemicals Co., St. Louis, Mo., USA) as the CCF were mixed with 50 μL of acetonitrile ("ACN"). The components were then milled using a ball-mill apparatus Retsch MM200 (GlenMills Inc, Clifton, N.J.) for 3 hours at the frequency of 15 Hz. The mixture was placed in the milling compartment made of sintered corundum. After milling, the material was moved in 20-mL screw cap scintillation vial (no cap) and dried in the vacuum for 16 hours at the room temperature. After drying, the cap was screwed on. The resulting material was off white-grayish color.

Oxalic Acid (OA): 70 mg of VX-950 and an equal molar equivalent of OA (Sigma Chemicals Co., St. Louis, Mo., USA) as the CCF were mixed with 5 μL of less of any of the following solvents (based on 10 mg total solids): ethyl acetate, methyl ethyl ketone, acetonitrile, water or 1,2-dichloroethane. The components were ground together. A co-crystal of VX-950 and OA was obtained after the same procedure as described above.

EXAMPLE 2

Preparation by Melting Method 100 mg of VX-950 and an equal molar equivalent of a CCF selected from the group consisting of salicylic acid, 4-amino salicylic acid, and oxalic acid (Sigma Chemicals Co., St. Louis, Mo., USA) were mixed by vortex for 5 minutes. This procedure was performed twice. Once it was performed without a solvent. At the second time, it was performed with 100 μL of acetonitrile, methyl ethyl ketone, and ethyl acetate for 4-amino salicylic acid, salicylic acid, and oxalic acid, respectively. The mixtures were placed in a reaction block (Radley Discovery Technologies, RR 98072) with the lid closed and heated to the endotherm. The mixtures were hold for 30 minutes at the endotherm temperature, and then the resulting mixture was cooled off under ambient conditions with the lid off, and the solvent, when used, removed.

EXAMPLE 3

Preparation by Solvent-Evaporation Method

VX-950 and a CCF selected from the group consisting of salicylic acid, 4-amino salicylic acid, and oxalic acid (Sigma Chemicals Co., St. Louis, Mo., USA) were dissolved separately into a solvent mixture of 50% toluene/acetonitrile. Dissolution was aided by rotation and sonication until visual clarity in the solutions was obtained. VX-950 solutions were mixed with CCF solutions in 20-mL screw cap scintillation vials at 0:1, 1:3, 1:1 and 3:1, 1:0 molar ratios in 3 mL final volumes for all. These vials were placed uncapped in a fume hood and solvents allowed to evaporate to dryness over a period of several days, to give a solid material.

EXAMPLE 4

Preparing by Modeling Method

The modeling also resulted in co-crystals of VX-950 and a CCF selected from the group consisting of salicylic acid, 4-amino salicylic acid, and oxalic acid (Sigma Chemicals Co., St. Louis, Mo., USA).

EXAMPLE 5

Thermogravimetric Analysis (TGA)

TGA of each sample was performed using a Model Q500 Thermogravimetric Analyzer (TA Instruments, New Castle, Del., USA), which uses its control Thermal Advantage Q Series™ software, Version 2.2.0.248, Thermal Advantage Release 4.2.1 (TA Instruments-Water LLC), with the following components: QAdv.exe version 2.2 build 248.0; RhDII-.dII version 2.2 build 248.0; RhBase.dII version 2.2 build 248.0; RhComm dII version 2.2 build 248.0; TaLicense.dII version 2.2 build 248.0; and TGA.dII version 2.2 build 248.0. In addition, the analysis software used was Universal Analysis 2000 software for Windows 2000/XP, version 4.1 D build 4.1.0.16 (TA Instruments).

For all of the experiments, the basic procedure for performing TGA included transferring an aliquot (about 3-8 mg) of a sample into a platinum sample pan (Pan: Part No. 952018.906, TA Instruments). The pan was placed on a loading platform and was then automatically loaded into the Q500 Thermogravimetric Analyzer using the control software. Thermograms were obtained by individually heating the sample at 10° C./minute across a temperature range (generally from the room temperature to 300° C. under flowing dry nitrogen (compressed nitrogen, grade 4.8 (BOC Gases, Murray Hill, N.J., USA), with a sample purge flow rate of 90 L/minute and a balance purge flow rate of 10 L/minute. Thermal transitions (e.g. weight changes) were viewed and analyzed using the analysis software provided with the instrument.

As in FIG. 1, TGA spectrum of the co-crystal of VX-950 and SA (molar ratio being 1) shows an approximate 2.3% weight loss up to 145° C. and a total of 18% weight loss up to 160° C. This is consistent with the expected loss of salicylic acid for a 1:1 co-crystal. The first weight loss is likely due to the sublimation of salicylic Acid, which begins to sublime at 76° C.

Figure 2:
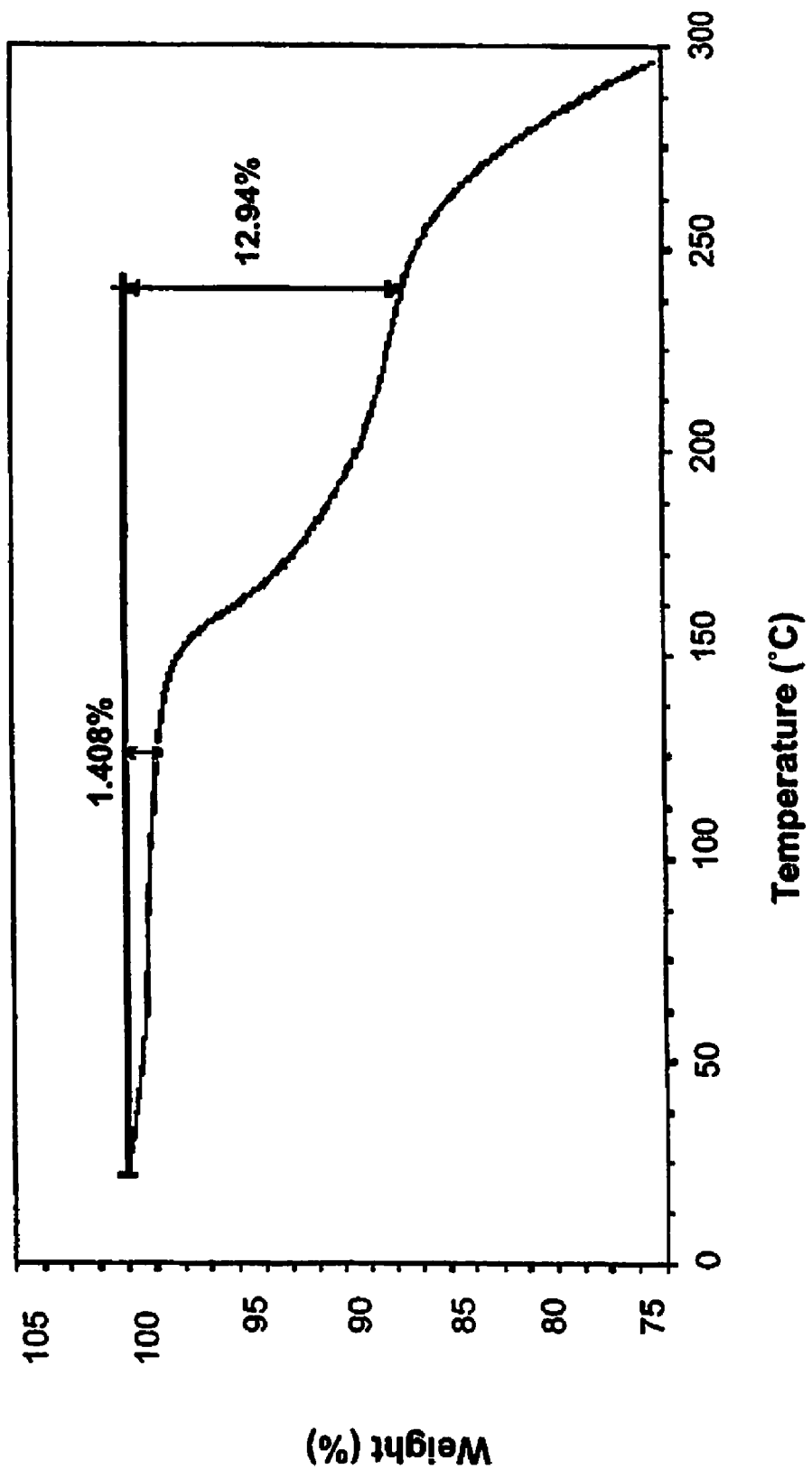
FIG. 2 shows a TGA spectrum of the co-crystal of VX-950 and 4-ASA.

As in FIG. 2, TGA spectrum of the co-crystal of VX-950 and 4-ASA (molar ratio also being 1) showed an approximate 1.4% weight loss up to 125° C. due to the solvent release and approximate 13% weight loss up to about 250° C.

EXAMPLE 6

Differential Scanning Calorimetry (DSC)

DSC analysis was performed using an MDSC Q100 Differential Scanning calorimeter (TA Instruments), which uses its control Thermal Advantage Q Series™ software, version 2.2.0.248, Thermal Advantage Release 4.2.1, with the following components: QAdv.exe version 2.2 build 248.0; RhDII.dII version 2.2 build 248.0; RhBase.dII version 2.2 build 248.0; RhComm.dII version 2.2 build 248.0; TaLicense.dII version 2.2 build 248.0; and DSC.dII version 2.2 build 248.0. In addition, the analysis software used was Universal Analysis 2000 software for Windows 2000/XP, version 4.1 D build 4.1.0.16 (TA Instruments). The instrument was calibrated with indium.

For all DSC analysis, an aliquot of a sample (approximately 2 mg) was weighed into an aluminum sample pan (Pan: Part No. 900786.901; and Lid: Part No. 900779.901, TA Instruments). The sample pan was closed by crimping with a single pinhole and then loaded into the Q100 Differential Scanning Calorimeter which was equipped with an autosampler. A thermogram was obtained by individually heating each sample at a rate of 10° C./minute across a temperature range (generally from the room temperature to 300° C.) under flowing dry nitrogen (compressed nitrogen, grade 4.8 (BOC Gases, Murray Hill, N.J., USA), with a sample purge flow rate of 60 L/minute and a balance purge flow rate of 40 L/minute. An empty aluminum pan prepared the same way as the pan with the sample was used a reference. Thermal transitions were viewed and analyzed using the analysis software provided with the instrument.

Figure 3:
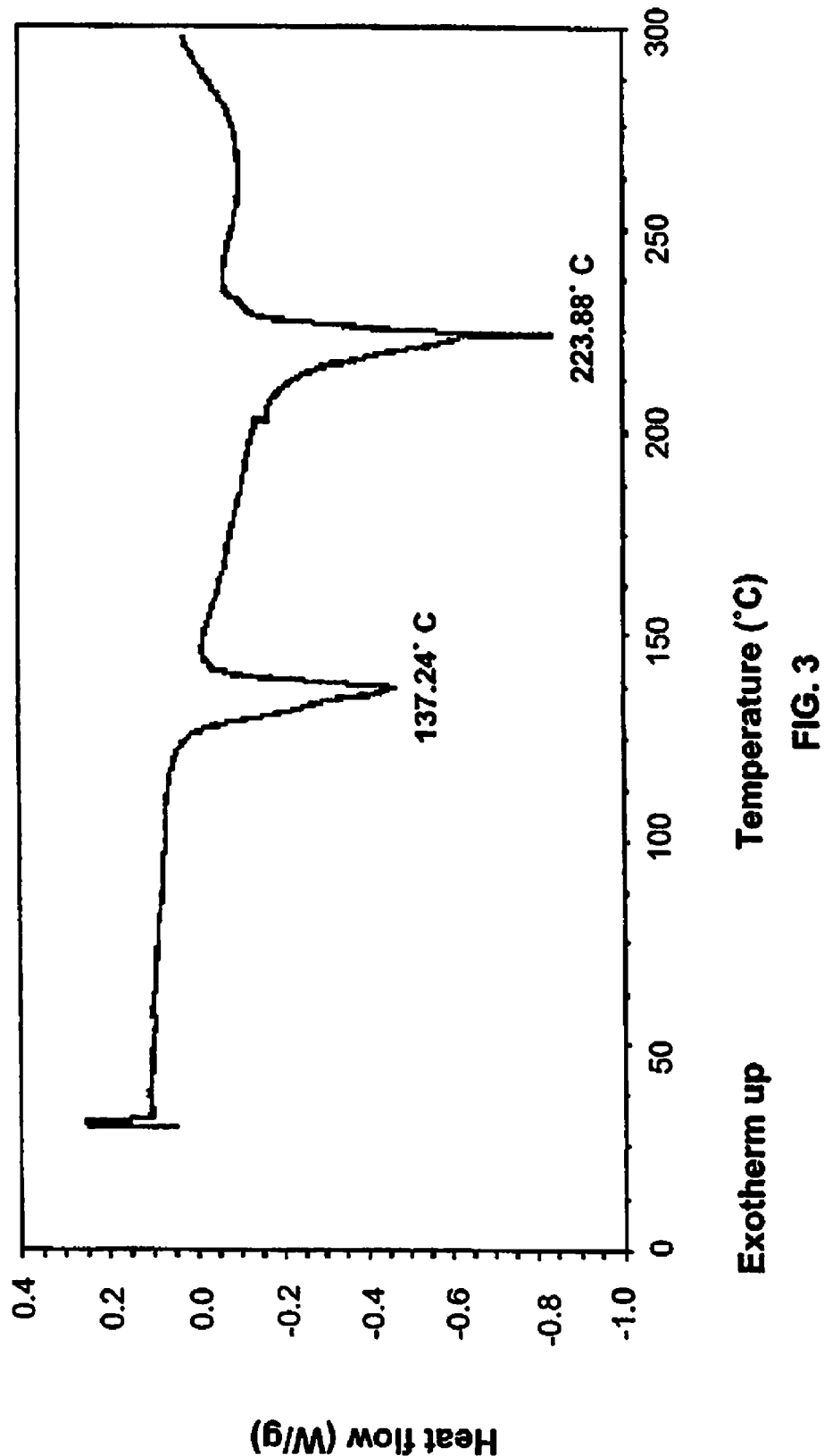
FIG. 3 shows a DSC thermogram of the co-crystal of VX-950 and SA.

As in FIG. 3, DSC thermogram shows the co-crystal of VX-950 and SA first melt at approximately 137° C. The melting points of SA and VX-950 are 159° C. and 247° C., respectively. The second melting transition at 223° C. corresponds roughly to that of the free compound. The lower melting is observed due to the impurity presence, but may include some decomposition.

Figure 4:
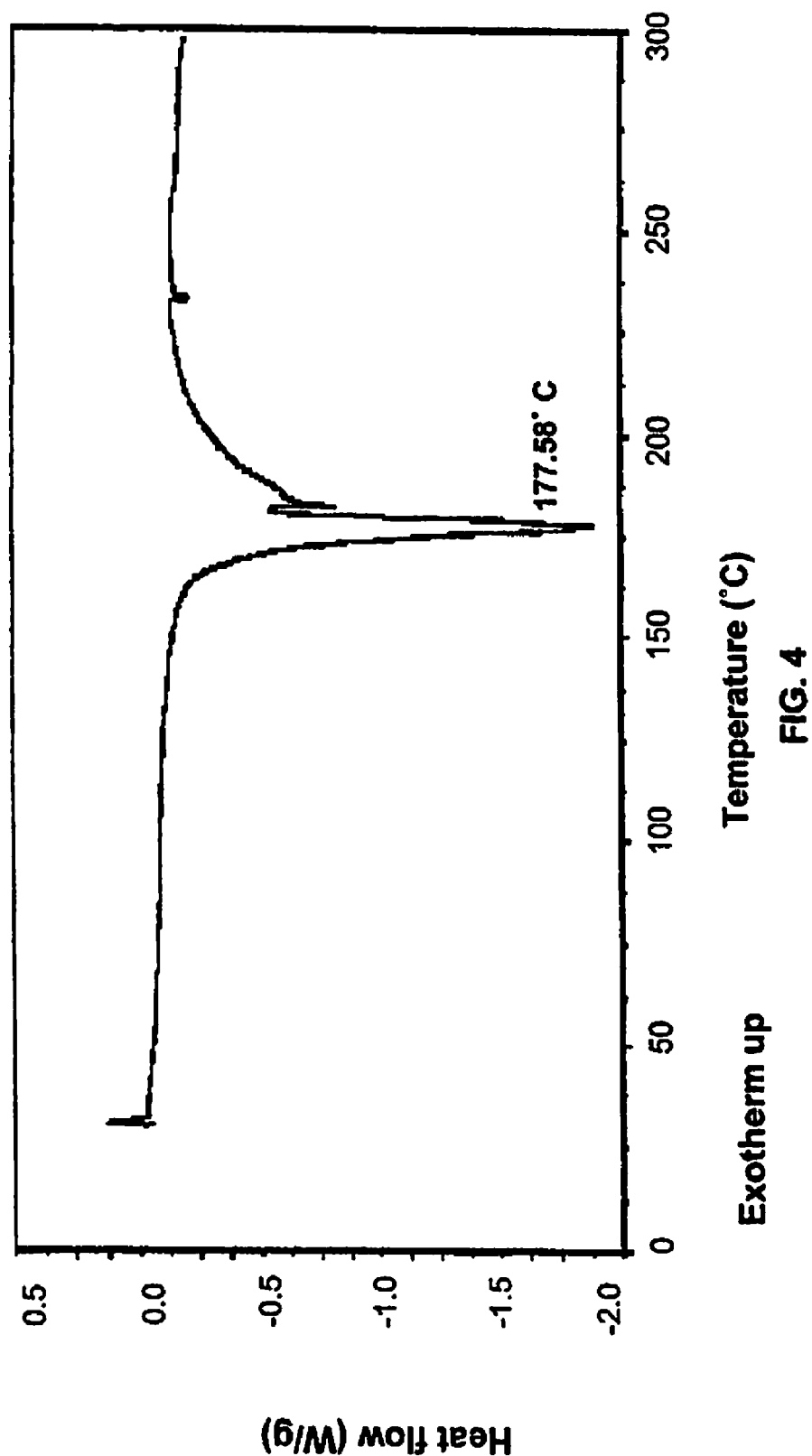
FIG. 4 shows a DSC thermogram of the co-crystal of VX-950 and 4-ASA.

As in FIG. 4, DSC thermogram shows the co-crystal of VX-950 and 4-ASA melt at about 177° C.

Table 1 below is a summary of DSC screen for potential interaction between VX-950 and a CCF used in this invention.

TABLE 1

| CCF | Endo, Tm co-former (° C.) | Endo, Tm possible eutectic (° C.) |
|---|---|---|
| 4-ASA | 134 | 167 |
| OA | 101 & 192 | — |
| SA | 159 & 176 | 122 |

EXAMPLE 7

X-Ray Powder Diffraction (XRPD)

In XRPD analysis, an instrument from either Bruker or Rigaku was used.

a. Bruker

The XRPD pattern was obtained at the room temperature in reflection mode by using a Bruker D8 Discover diffractometer that was equipped with a sealed tube source and a Hi-Star area detector (Bruker AXS, Madison, Wis., USA). A copper target X-ray tube (Siemens) was operated at 40 kV and 35 mA. Graphite monochromator and 0.5 mm collimator provided by Bruker were used to produce parallel, monochromatic beam (CuKa, 1=1.5418 Å). The distance between the sample and the detector was approximately 30 cm. The sample was placed on a Si zero-background wafer (The Gem Dugout, State College, Pa.) which was then positioned and centered on XYZ platform. Data were acquired using GADDS software for Windows NT, version 4.1.16 (Bruker AXS, Madison, Wis., USA). Two frames were registered with an exposure time of 120 seconds per frame. The sample was oscillated in both X and Y directions with an amplitude of 1 mm during the exposure. The data were subsequently integrated over the range of 3° to 41° 2-Theta with a step size of 0.02° and merged into one continuous pattern. Corundum plate (NIST standard 1976) was used to calibrate the instrument.

b. Rigaku

The XRPD pattern was recorded at the room temperature in transmission mode using a rotating anode RUH3R X-ray generator (Rigaku, The Woodlands, Tex., USA) and a Rigaku Raxis IIC detector. Radiation of CuK at 50 kV and 100 mA was used. Focusing minors and a Ni filter were used to produce parallel, monochromatic beam (1=1.5418 Å). The sample was held in a 2 mm diameter boron glass capillary (Hampton Research, Aliso Viejo, Calif., USA) and was rotated around the f axis during the experiment. The distance between the sample and the detector was approximately 25 cm. A single frame with an exposure time of 300 seconds was recorded using CrystalClear software, Version 1.3.5 SP2 by Rigaku. The data were subsequently integrated over the range of 3° to 40° 2q with a step size of approximately 0.02°. Silicon powder (NIST standard 640c) was used to calibrate the instrument.

Figure 5:
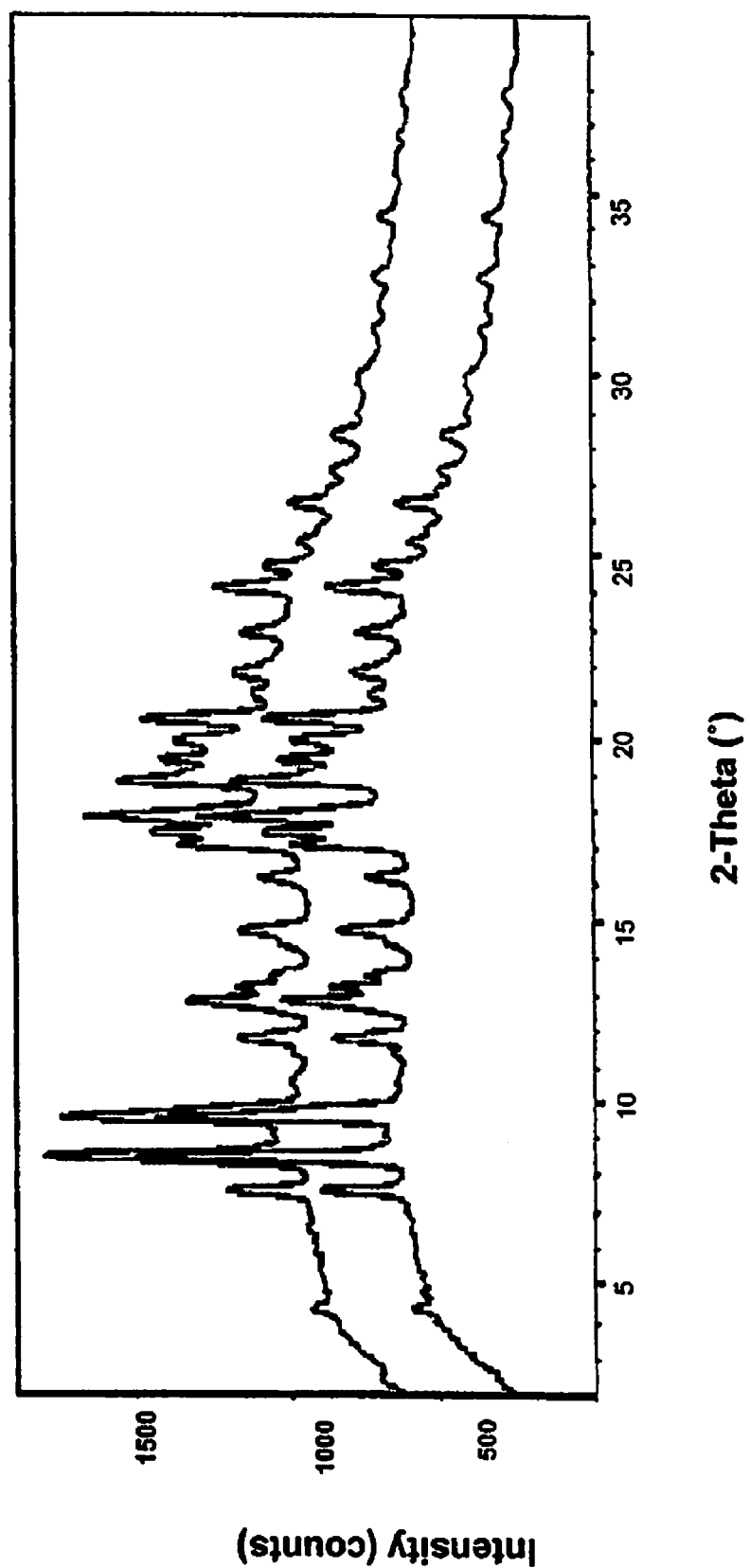
FIG. 5 shows XRPD spectra of the co-crystal of VX-950 and 4-ASA in water (upper) and 1% HPMC (lower) in 6 hours at room temperature.

As shown in FIG. 5, in water and in 1% hydroxypropylmethylcellulose (HPMC) at the room temperature after 6 hours, the co-crystal of VX-950 and 4-ASA showed no sign of conversion to the free form after incubation times of up to 6 hours. At the 24-hour time point, the co-crystal was still intact in the 1% HPMC solution. However, in water the sample had converted back to the free form at the 24 hour time point.

Figure 6:
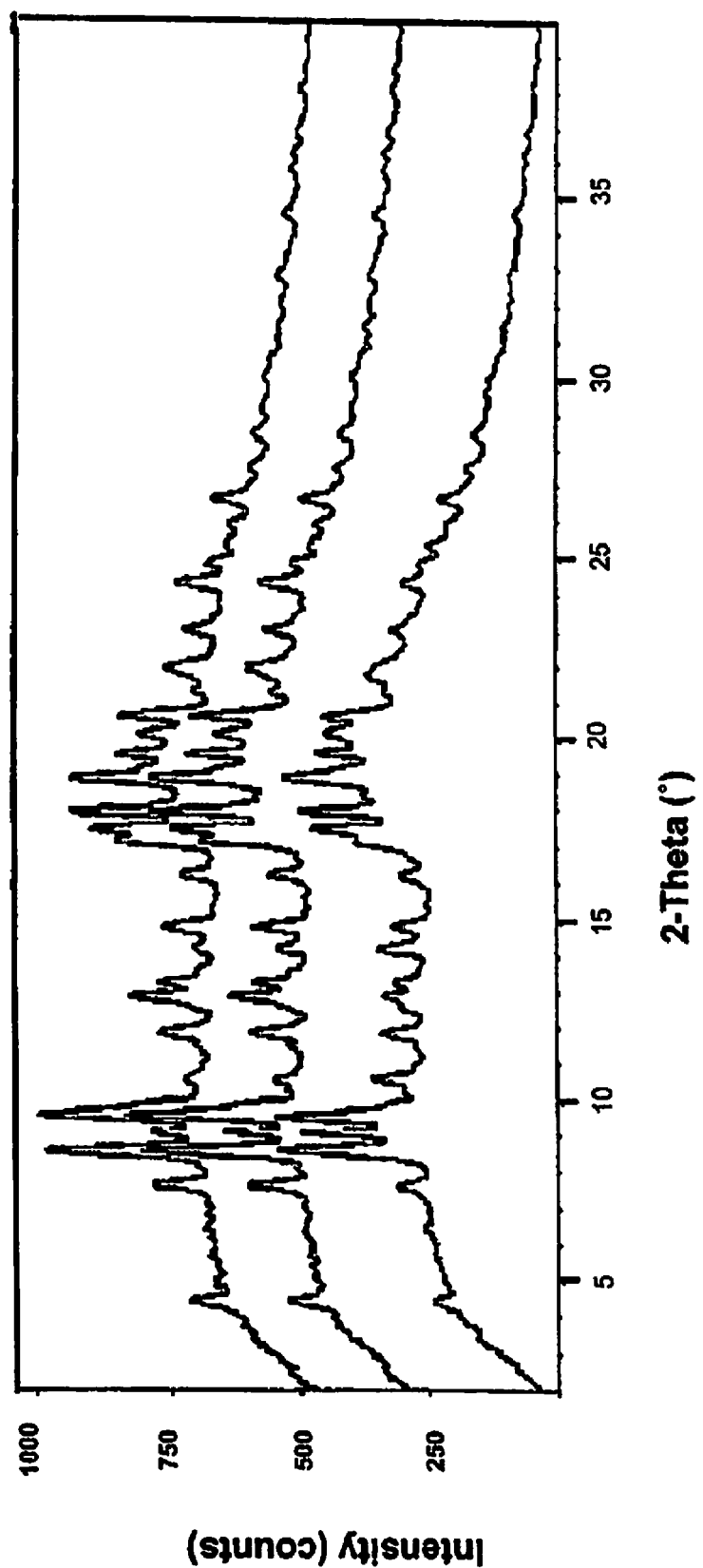
FIG. 6 shows XRPD spectra of the co-crystal of VX-950 and SA in water in 1 hour (upper), 2 hours (middle), and 6 hours (lower) at room temperature.
Figure 7:
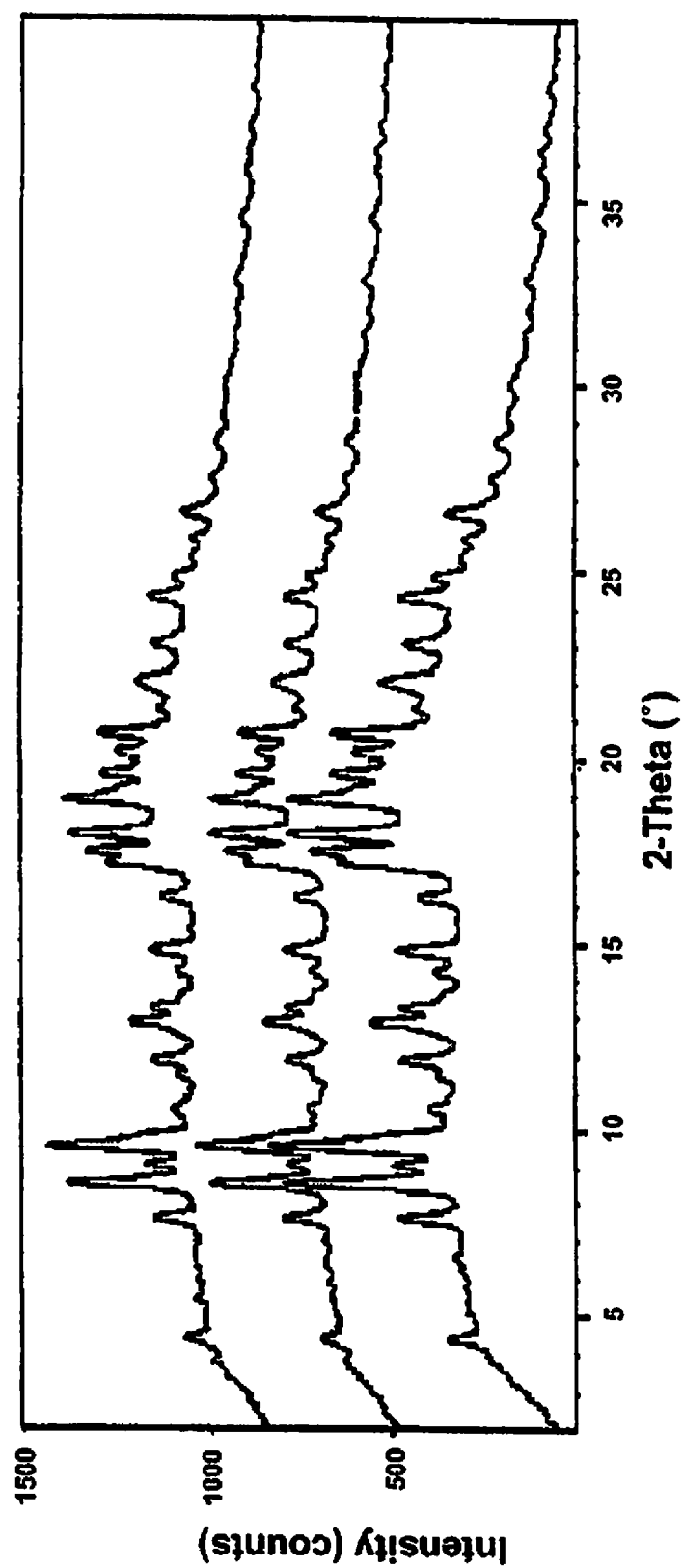
FIG. 7 shows XRPD spectra of the co-crystal of VX-950 and SA in 1% HPMC in 1 hour (middle), 2 hours (upper), and 6 hours (lower) at the room temperature.

By contrast, as shown in FIG. 6, the XRPD patterns of the co-crystal of VX-950 and SA, after suspension in water at room temperature, (i) after 1 hour, show a slight conversion from the co-crystal to the free from as indicated by the growth of the peak at 9.1 2-Theta(°), (ii) at the 2-hour time point, show additional conversion, and (iii) at the 6-hour time point, show complete conversion. After suspension in an aqueous solution of 1% HPMC, the same co-crystal shows slight conversion from the co-crystal to the free from at the 1-hour and 2-hour time point, and additional conversion at the 6-hour time point is observed. See FIG. 7.

Figure 8:
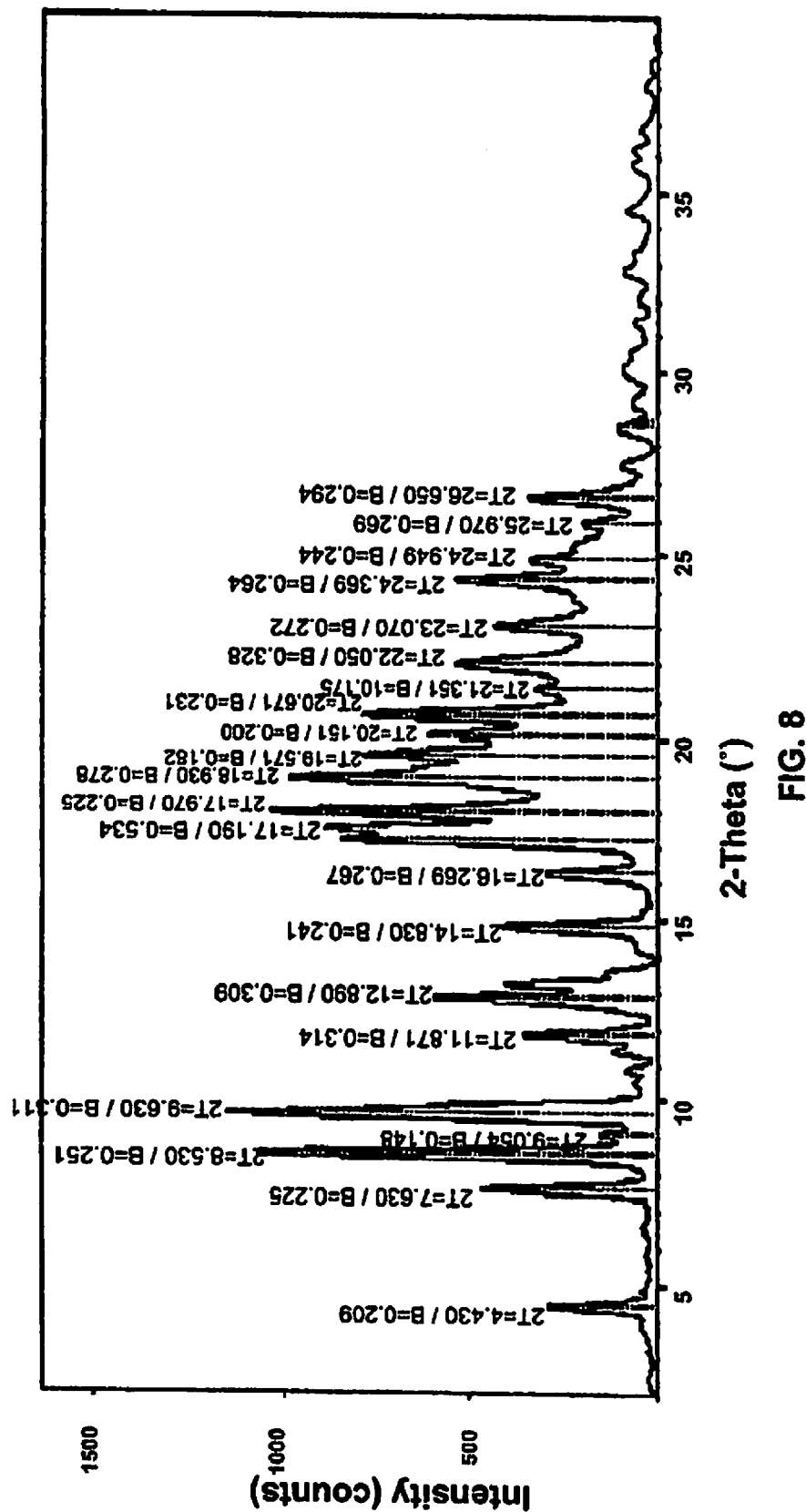
FIG. 8 shows an XRPD spectrum of the co-crystal between VX-950 and SA.
Figure 9:
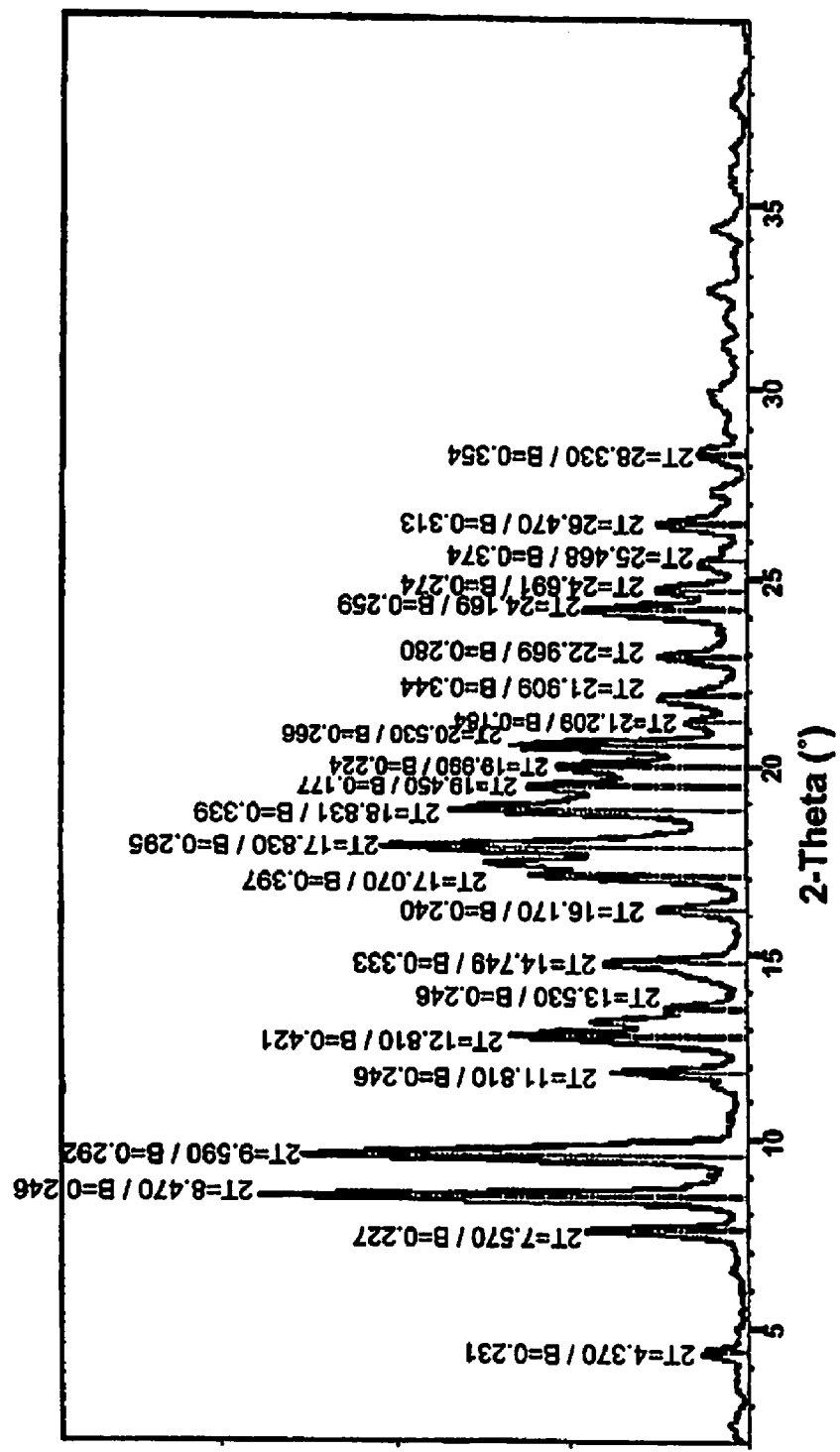
FIG. 9 shows an XRPD spectrum of the co-crystal of VX-950 and 4-ASA.
Figure 10:
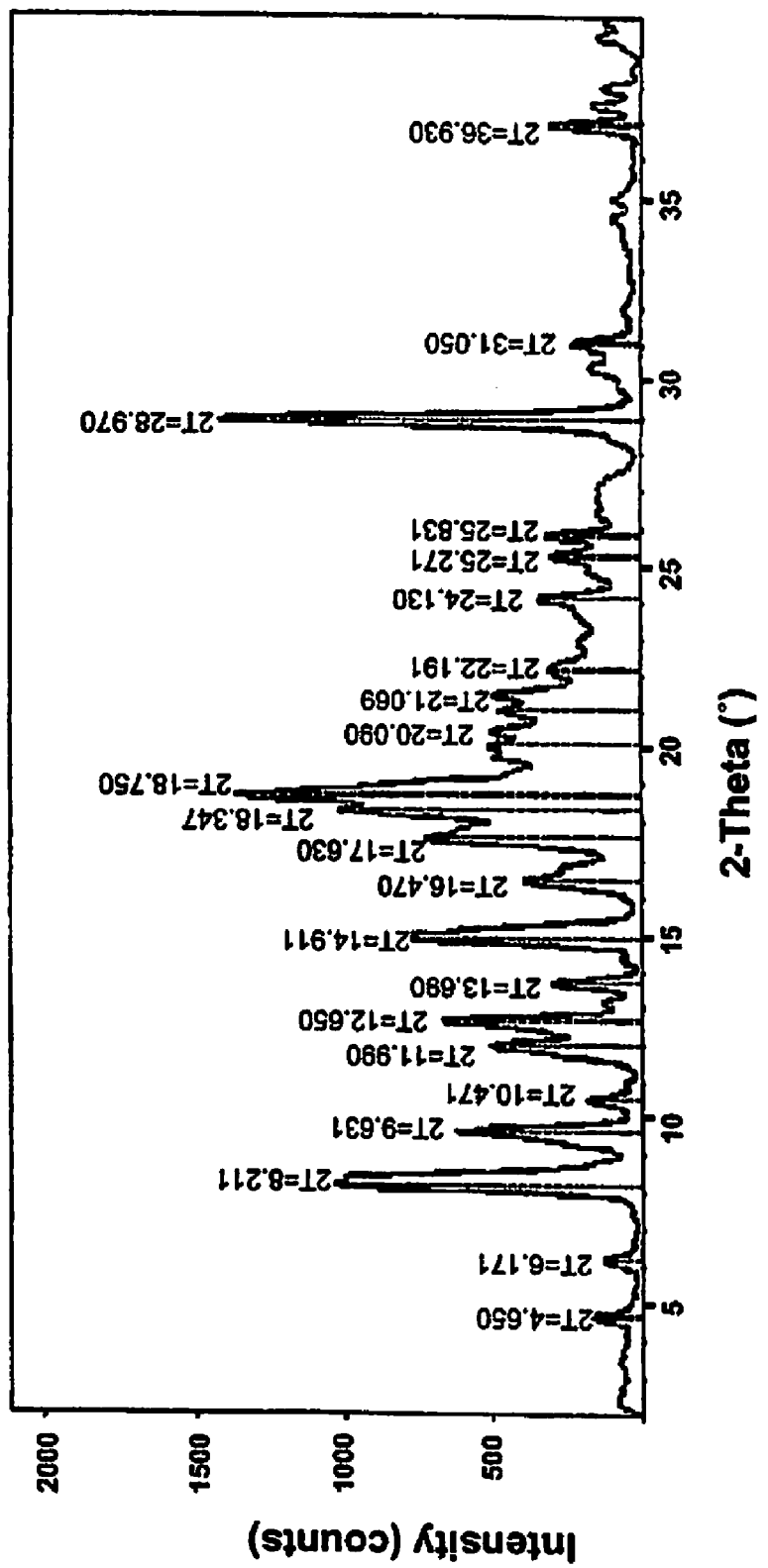
FIG. 10 shows an XRPD spectrum of the co-crystal of VX-950 and OA.

FIG. 8, FIG. 9, and FIG. 10 are the XRPD spectra of VX-950 co-crystals of SA, 4-ASA, and OA, respectively. Specifically, the co-crystal of VX-950 and SA shows XRPD peaks at 4.43, 7.63, 8.53, 9.63, 12.89, 14.83, and 16.29 2-Theta; the co-crystal of VX-950 and 4-ASA show XRPD peaks at 4.37, 7.57, 8.47, 9.59, 12.81, and 14.75 2-Theta; and the co-crystal of VX-950 and OA shows XRPD peaks at 4.65, 6.17, 8.21, 9.63, 12.65, 14.91, and 28.97 2-Theta.

EXAMPLE 8

Solubility Analyses

An aliquot of the sample was placed in a tube and then an aqueous medium was added. At set time points, an aliquot of supernatant was withdrawn, filtered through 0.45 PTFE micron filter (Millex, LCR, Millipore) and processed for high performance liquid chromatography (HPLC) analysis (Agilent 1100; Palo Alto, Calif., USA). The system was equipped with an autosampler set at 25° C. For the sample handling, an aliquot of the sample was diluted with acetonitrile at 1 to 1 by v/v ratio. The samples were run isocratically with the detector set at 270 nm. The column was XTerra® Phenyl column 150 mm×4.6 mm, 3.5 µm Particle Size (P/N 186001144) (Waters, Milford, Mass., USA). The mobile phase was potassium phosphate buffer (10 mM, pH=7.0):methanol at 60:40 (v/v) ratio. The run was done at the flow-rate of 1 mL/min and was completed within 15 min. Table 2 below summarized the solubilities of VX-950 and its co-crystal with 4-ASA in simulated intestinal fluid (pH 6.8) at 24-h time point at room temperature (expressed in VX-950 equivalents (VX-950 eluted at 8.8 minutes)).

TABLE 2

| System | C, mg/mL Control | C, mg/mL Melt | XRPD |
|---|---|---|---|
| VX-950 alone | 0.025 | | Amorphous (up to 2 hours at room temp.) |
| | 0.0183 | | Starts crystallizing by about 4 hours at room temp. |
| | Not Detected | | Crystallizes by 24 hour |
| VX-950 and 4-ASA | | 0.148 | Crystalline up to 24 hrs. No changes |

EXAMPLE 9

Suspension Stability

The physical stability of the co-crystal upon suspension in aqueous media was evaluated. The co-crystal powder was slurried in (1) unbuffered, deionized water and (2) a 1% (w/w) solution of HPMC (low viscosity grade) at 25° C. at a nominal concentration of approximately 6 mg/ml. Slurries were mixed using a magnetic stir bar and plate. The samples of the solid were isolated by filtration at time intervals of 1, 2, 6 and 24 hours.

PXRD patterns of co-crystal of VX-950 and salicylic acid, after suspension in water for 1, 2, and 6 hours, show a slight conversion from the co-crystal to the free form after one hour as indicated by the growth of the peak at 9.1 2-Theta(°). Additional conversion is observed at the 2-hour time point and complete conversion is found at the 6-hour time point.

PXRD patterns of co-crystal of VX-950 and salicylic acid, after suspension in an aqueous solution of 1% HPMC at 1, 2, and 6 hours, indicate that the co-crystal underwent slight conversion from the co-crystal to the free from at the one-hour and 2-hour time points. Additional conversion at the 6 hour time point is observed. The HPMC appears to have decreased the conversion rate of the co-crystal to the free form. The slow conversion is also evidenced by the growing peak at 9.1 2-Theta(°).

PXRD patterns of co-crystal of VX-950 and 4-amino salicylic acid, after suspension in water and an aqueous solution of 1% HPMC at 6 hours. In both cases, the co-crystal showed no sign of conversion to the free form after incubation times of up to 6 hours. At the 24-hour time point, the co-crystal is still intact in the 1% HPMC solution. However, in water, the sample had converted back to the free form at the 24-hour time point.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A co-crystal comprising (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide and 4-amino salicylic acid, wherein said co-crystal has X-ray powder diffraction peaks at about 4.37, 7.57, 8.47, 9.59, 12.81, and 14.75 2-Theta.

2. The co-crystal of claim 1, wherein the molar ratio of (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide and 4-amino salicylic acid is about 1:1.

3. The co-crystal of claim 2, having a DSC peak in its DSC thermogram at about 177° C.

4. A co-crystal of the formula (1S,3aR,6aS)-2-[(2S)-2-[[(2S)-2-Cyclohexyl-2-(pyrazine-2-carbonylamino)acetyl] amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide)$_m$:(CCF)$_n$, wherein CCF is 4-amino salicylic acid, and m and n, independently, are an integer of 1 to 5; and said co-crystal has X-ray powder diffraction peaks at about 4.37, 7.57, 8.47, 9.59, 12.81, and 14.75 2-Theta.

5. The co-crystal of claim 4, wherein m and n are both 1.

6. A pharmaceutical composition comprising a co-crystal comprising (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide and the co-crystal former 4-amino salicylic acid, wherein said co-crystal has X-ray powder diffraction peaks at about 4.37, 7.57, 8.47, 9.59, 12.81, and 14.75 2-Theta.

7. The pharmaceutical composition of claim 6, wherein (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide and the co-crystal former are together in the crystalline form.

8. The pharmaceutical composition of claim 6, wherein the molar ratio of (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide and the co-crystal former is about 1.

9. The pharmaceutical composition of claim 7, further comprising a diluent, solvent, excipient, carrier, or solubilizing agent.

10. A method of making a co-crystal comprising:
   a. providing (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide,
   b. providing a co-crystal former comprising 4-amino salicylic acid,
   c. grinding, heating, co-subliming, co-melting, or contacting in solution (1S,3aR,6aS)-2-[(2S)-2-[[(2S)-2-Cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-1-carboxamide with the co-crystal former under crystallization condition so as to form the co-crystal in solid phase, wherein said co-crystal has X-ray powder diffraction peaks at about 4.37, 7.57, 8.47, 9.59, 12.81, and 14.75 2-Theta, and
   d. optionally isolating the co-crystal formed by step (c).

* * * * *